US006972170B1

(12) United States Patent
Cordon-Cardo et al.

(10) Patent No.: US 6,972,170 B1
(45) Date of Patent: Dec. 6, 2005

(54) MARKERS FOR PROSTATE CANCER

(75) Inventors: Carlos Cordon-Cardo, New York, NY (US); Howard I. Scher, Tenafly, NJ (US); Andrew Koff, Westbury, NY (US)

(73) Assignee: Sloan-Kettering Institute for Cancer Research, New York, NY (US)

( * ) Notice: Subject to any disclaimer, the term of this patent is extended or adjusted under 35 U.S.C. 154(b) by 0 days.

(21) Appl. No.: 09/329,917

(22) Filed: Jun. 10, 1999

Related U.S. Application Data

(63) Continuation-in-part of application No. PCT/US98/25483, filed on Dec. 1, 1998.
(60) Provisional application No. 60/067,190, filed on Dec. 1, 1997.

(51) Int. Cl.[7] .......................... C12Q 1/68; G01N 33/53; C12P 19/34
(52) U.S. Cl. ...................... 435/6; 435/7.1; 435/91.1; 435/91.2
(58) Field of Search ................... 435/6, 91.1, 91.2, 435/7.1

(56) References Cited

U.S. PATENT DOCUMENTS

| 5,688,665 A | 11/1997 | Massague et al. |
| 6,316,208 B1 * | 11/2001 | Roberts et al. ............ 435/7.21 |
| 2004/0053247 A1 | 3/2004 | Cordon-Cardo et al. |

FOREIGN PATENT DOCUMENTS

| WO | WO 9422478 | 10/1994 |
| WO | WO 9833450 | 8/1998 |
| WO | WO 9904238 | 1/1999 |
| WO | WO 9928749 | 6/1999 |
| WO | WO 9931140 | 6/1999 |
| WO | WO 0077258 | 12/2000 |

OTHER PUBLICATIONS

Agus, D.B., et al., (1999) "Response of Prostate Cancer to Anti–Her–2/neu Antibody in Androgen–dependent and – independent Human Xenograft Models", *Cancer Res.* 59:4761–4764. (Exhibit 2).
Agus, D.B. et al., (1999) "Prostate Cancer Cell Cycle Regulators: Response to Androgen Withdrawal and Development of Androgen Independence", *J. Natl. Cancer. Inst.* 91:1869–1876. (Exhibit 3).
Aprikian, A.G., et al., (1994) "Immunohistochemical Determination of P53 Protein Nuclear Accumulation in Prostatic Adenocarcinoma", *Jrnl. of Urol.* 151:1276–1280. (Exhibit 4).
Campbell, M.J., et al., (1997) "Inhibition of proliferation of prostate cancer cells by a 19–nor–hexafluoride vitamin $D_3$ analogue involves the induction of $p21^{waf1}$, $p27^{kip1}$ and E–cadherin", *Journal of Molecular Endocrinolgy* 19:15–27. (Exhibit 5).

Cohen, D.W., et al., (1994) "Expression of Transforming Growth Factor–α and the Epidermal Growth Factor Receptor in Human Prostate Tissues", *J. Urol.* 152:2120–2124. (Exhibit 6).
Cordon–Cardo C., et al., (1998) "Distinct Altered Patterns of $p27^{KIP1}$ Gene Expression in Benign Prostatic Hyperplasia and Prostatic Carcinoma", *J. Natl. Cancer Inst.* 90:1284–1291, (Exhibit 7).
Cote, R.J., et al., (1998) "Association of $p27^{Kip1}$ Levels With Recurrence and Survival in Patients With Stage C Prostate Carcinoma",*J. Natl. Cancer Inst.* 90(12): 916–920. (Exhibit 8).
Di Cristofano, A., et al., (1998) "Pten is essential for embryonic development and tumour suppression", *Nature Genetics* 19:348–355. (Exhibit 9).
Hengst, L., et al., (1996) "Translational Control of $p27^{Kip1}$ Accumulation During the Cell Cycle", *Science* 271:1861–1864. (Exhibit 11).
Knudsen, K.E., et al., (1998) "Multiple $G_1$ Regulatory Elements Control the Androgen–dependent Proliferation of Prostatic Carcinoma Cells",*Journal of Biological Chemistry* 273 (32): 20213–20222. (Exhibit 12).
Kokontis, J.M., et al., (1998) "Progression of LNCaP Prostate Tumor Cells During Androgen Deprivation: Hormone–Independent Growth, Repression of Proliferation by Androgen, and Role for $p27^{Kip1}$ in Androgen–Induced Cell Cycle Arrest", *Molecular Endocrinology,* 12:941–953. (Exhibit 13).
Lacombe, L., et al., (1996) "Microsatellite Instability and Deletion Analysis of Chromosome 10 in Human Prostate Cancer", *Int. J. Cancer* 69:110–113. (Exhibit 14).
Lee, C.T., et al., (1999) "Overexpression of the Cyclin–dependent Kinase Inhibitor p16 is Associated with Tumor Recurrence in Human Prostate Cancer[1]", *Clin. Cancer Res.* 5:977–983. (Exhibit 15).
Osman, I., et al., (1997) "Chromosome 16 in Primary Prostate Cancer: A Microsatellite Analysis", *Int. J. Cancer* 71:580–584. (Exhibit 16).

(Continued)

*Primary Examiner*—Jehanne Sitton
(74) *Attorney, Agent, or Firm*—John P. White; Cooper & Dunham LLP

(57) ABSTRACT

This invention provides a method for determining the aggressiveness of a prostate carcinoma comprising: (a) obtaining a sample of the prostate carcinoma; and (b) detecting the presence of p27 protein in the prostate carcinoma, the absence of p27 indicating that the prostate carcinoma is aggressive. This invention also provides a method for diagnosing a beign prostate hyperplasia comprising: (a) obtaining an appropriate sample of the hyperplasia; and (b) detecting the presence of the p27 RNA, a decrease of the p27 RNA indicating that the hyperplasia is beign. This invention provides various uses of p27 in prostate cancer. Finally, this invention also provides different marker for prostate cancer.

2 Claims, 12 Drawing Sheets

OTHER PUBLICATIONS

Osman, I., et al., (1999) "Inactivation of the p53 Pathway in Prostate Cancer: Impact on Tumor Progression[1]", *Clinical Cancer Research* 5:2082–2088. (Exhibit 17).

Ponce–Castaneda, M.V., et al., (1995) "p27$^{Kip1}$: Chromosomal Mapping to 12p12–12p13.1 and Absence of Mutations in Human Tumors". *Cancer Research* 55:1211–1214. (Exhibit 18).

Polyak, K., et al., (1994) "Cloning of p27$^{Kip1}$, a Cyclin–Dependent Kinase Inhibitor and a Potential Mediator of Extracellular Antimitogenic Signals", *Cell* 78:59–66. (Exhibit 19).

Polyak, K., et al., (1994) "p27$^{Kip1}$, a Cyclin–Cdk Inhibitor, links transforming growth factor–$\beta$ and contact inhibition to cell cycle arrest", *Genes & Development* 8:9–22. (Exhibit 20).

Scher, H.I., et al., (1995) "Changing Pattern of Expression of the Epidermal Growth Factor Receptor and Transforming Growth Factor $\alpha$ in the Progression of Prostatic Neoplasms[1]", *Clinical Cancer Research* 1:545–550. (Exhibit 21).

Silver, D.A., et al., (1997) "Prostate–specific Membrane Antigen Expression in Normal and Malignant Human Tissues[1]", *Clinical Cancer Research* 3:81–85. (Exhibit 22).

Simak, R., et al., (2000) "Expression of c–kit and kit–ligand in benign and malignant prostatic tissues", *Histol Histopathol* 15:365–374. (Exhibit 23).

Lloyd, et al., (1999) "A multifunctional cyclin–dependent kinase inhibitor with prognostic significance in human cancers", *American Journal Pathology*, 154(2):313–323. (Exhibit 1).

DeMarzo, A.M., et al. (1998) "Prostate Stem Cell Compartments: Expression of the Cell Cycle Inhibitor P27kip1 in Normal, Hyperplastic, and Neoplastic Cells" *Amer. J. Path.* 153(3): 911–919 (Exhibit 3).

Fernandez, P.L. et al. (1999) "Expression of p27/kip1 is down–regulated in human prostate carcinoma progression" *J. Path.* 187(5): 563–566 (Exhibit 4).

McArthur, J.G. et al. (1999) "Cancer Gene Therapy with Novel Chimeric P27/p16 Tumor Suppressor Genes" *Proceed. Amer. Assoc. Cancer Res. Ann.* 40: 630 (Exhibit 5).

Aaltomaa, S. et al. (1999) "Prognostic Value and Expression of p21 (waf1/cip1) Protein in Prostate Cancer" *The Prostate*, 39(1):8–15 (Exhibit 3).

Arai, Y. et al., (1997) "C–erbB–2 Oncoprotein: A Potential Biomarker of Advanced Prostate Cancer" *Prostate*, 30(3):195–201 (Exhibit 4).

Baretton, G.B. et al. (1999) "Proliferation– and Apoptosis–Associated Factors in Advanced Prostatic Carcinomas Before and After Androgen Deprivation Therapy: Prognostic Significance of p21/WAF1/CIP1 Expression" *British Journal of Cancer*, 80(3–4):546–555 (Exhibit 5).

Baselga, J. et al., (1998) "Recombinant Humanized Anti-HER2 Antibody (Herceptin TM) Enhances the Antitumor Activity of Paclitaxel and Doxorubicin Against HER2/neu Overexpressing Human Breast Cancer Xenografts" 58(13):2825–2831 (Exhibit 6).

Cariou S. et al. (1998) "Prognostic Implication of Expression of the Cell Cycle Inhibitor Protein P27", *Breast Cancer Research and Treatment*, 1–3(52):29–41 (Exhibit 7).

Chen, Y. et al. (1998) "Increased Cell Growth and Tumorigenicity in Human Prostate LNCaP Cells by Overexpression to Cyclin D1" *Oncogene*, 16(15):1913–1920 (Exhibit 8).

Craft, N. et al., (1999) "A Mechanism for Hormone–Independent Prostate Cancer Through Modulation of Androgen Receptor Signaling by the HER–2/neu tyrosine Kinase" *Nature Medicine*, 5(3):280–285 (Exhibit 9).

Curnow, R.T. et al., (1997) "Clinical Experience With CD64–Directed Immunotherapy. An Overview" *Cancer Immunology And Immunotherapy*, 45(3–4):210–15 (Exhibit 10).

Gumbiner, L. et al. (1999) "Overexpression of Cyclin D1 Is Rare in Human Prostate Carcinoma" *Prostate*, 38(1):40–45 (Exhibit 12).

Han, E. et al., (1998) "Cyclin D1 Expression in Human Prostate Carcinoma Cell Lines and Primary Tumors" *Prostate*, 35(2):95–101 (Exhibit 13).

James, N. et al., (1998) "Phase II Trial of the Bispecific Antibody MDX–H210 (Anti–Her2/Neu X Anti–CD64) Combined With GM–CSF In Patients With Advanced Prostate and Renal Cell Carcinomas That Express Her2/Neu" *British Journal of Cancer*, 78(Suppl 2):19 (Exhibit 14).

Koeneman, K.S. et al., (1999) "Osteomimetic Properties of Prostate Cancer Cells: A Hypothesis Supporting the Predilection of Prostate Cancer Metastasis and Growth in the Bone Environment" *Prostate*, 39:246–261 (Exhibit 15).

Ross, J.S. et al., (1993) "Contribution of HER–2/neu Oncogene Expression to Tumor Grade and DNA Content Analysis in the Prediction of Prostatic Carcinoma Metastasis" *Cancer*, 72(10):3020–3028 (Exhibit 16).

Veltri, R. et al. (1994) "Quantitative nuclear morphometry, Markovian Texture Descriptors, and DNA content Captured on a CAS–200 Image Analysis Systems, Combined With PCNA and HER–2/neu Immunohistochemistry for Prediction of Prostate Cancer Progression" *Journal of Cellular Biochemistry*, 19:249–258 (Exhibit 17).

Yamasaki, I. et al. (1996) "Overexpression of MDM2 and p53 Protein is Infrequently but Significantly Associated With Progression of Human Prostatic Adenocarcinoma" *Oncology Reports*, 3(5):925–929 (Exhibit 18); and.

Zhau, H. et al. (1992) "Expression of C–erb B–2/neu Proto–Oncogene in Human Prostatic Cancer Tissues and Cell Lines" *Molecular Carcinogenesis*, 5(4): 320–327 (Exhibit 19).

DeMarzo, A.M., et al. (1998) "Prostate Stem Cell Compartments: Expression of the Cell Cycle Inhibitor P27kip1 in Normal, Hyperplastic, and Neoplastic Cells" *Amer. J. Path.* 153(3): 911–919 (Exhibit 3).

Fernandez, P.L. et al. (1999) "Expression of p27/kip1 is down–regulated in human prostate carcinoma progression" *J. Path.* 187 (5): 563–566 (Exhibit 4).

Guo, Y., et al. (1997) "Loss of the Cyclin–dependent Kinase Inhibitor p27$^{Kip1}$ Protein in Human Prostate Cancer Correlates with Tumor Grade[1]" *Clin. Cancer Res.* 3: 2269–2274.

McArthur, J.G. et al. (1999) "Cancer Gene Therapy with Novel Chimeric P27/p16 Tumor Suppressor Genes" *Proceed. Amer. Assoc. Cancer Res. Ann.* 40: 630 (Exhibit 5).

U.S. Appl. No. 10/009,861, filed Dec. 10, 2001, on behalf of Sloan–Kettering Institute for Cancer Research, national stage of PCT International Application No. PCT/US00/16007, filed Jan. 2, 2001, International Publication No. WO00/77258, published Dec. 21, 2000, including a copy of the pending claims (Exhibit 3).

Database Biosis [Online] Biosciences Information Service, Philadelphia, PA, US (Mar. 1999) Lee Tae Yoon et al., "Immunohistochemical Expression of p53 and MDM–2 Protein in Various Epithelial Carcinomas" Database Accession No. PREV1999900406745 (Exhibit 5).

\* cited by examiner

FIGURE 8A
FIGURE 8B

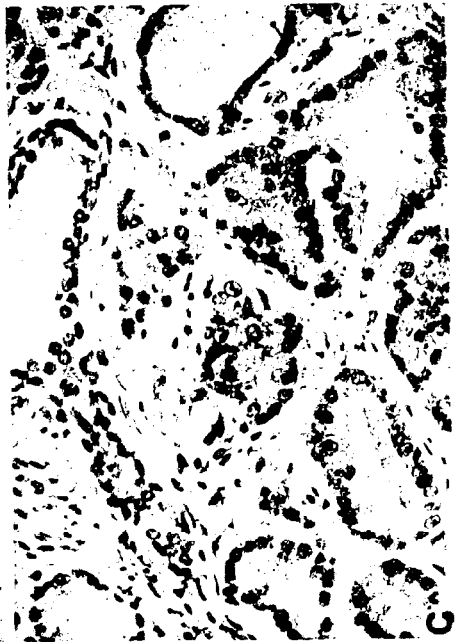
FIGURE 9A
FIGURE 9B
FIGURE 9C
FIGURE 9D

MARKERS FOR PROSTATE CANCER

This application is a Continuation-In-Part application of International Application No. PCT/US98/25483, filed Dec. 1, 1998, which claims the benefit of U.S. Provisional Application No. 60/067,190, filed Dec. 1, 1997, the content of which are incorporated into this application by reference.

This invention was made in part with support under United States Government NIH Grant CA-DK-47650. Accordingly, the United States Government has certain rights in the invention.

Throughout this application, various references are referred to within parentheses. Disclosures of these publications in their entireties are hereby incorporated by reference into this application to more fully describe the state of the art to which this invention pertains. Full bibliographic citation for these references may be found at the end the specification, preceding the claims.

BACKGROUND OF THE INVENTION

It has been postulated that the loss of function of a new family of negative cell cycle regulators, which act as cyclin-dependent kinase inhibitors and have been termed CKI, might lead to tumor development. CKIs fall into two families, Kip and Ink, on the basis of sequence homology. $p27^{Kip1}$ is implicated in G1 phase arrest by associating with multiple G1 cyclin-dependent kinases, abrogating their activity. However, no tumor-specific $p_{27}^{Kip1}$ genomic mutations have been found in a large group of primary human cancers studied. More recently, it has been reported that proteasome-mediated degradation of p27 protein occurs during the cell cycle and that this degradation is increased in a subset of breast and colon carcinomas of poor prognosis. Purpose: The present study was undertaken in order to assess for potential alterations of p27 expression in benign prostatic hyperplasia (BPH) and in a well characterized cohort of patients with prostatic cancer.

Inactivation of the p53 and RB tumor suppressor genes has been implicated in the development and progression of a number of different cancers (1,2). It has been also postulated that the loss of function of a new family of negative cell cycle regulators, which act as cyclin-dependent kinase inhibitors and have been termed CKI, might also lead to tumor development (3). CKIs fall into two families, Kip and Ink, on the basis of sequence homology (4). Kip family members include p21 (also known as WAF1, Cip1, or Sdi1) (5–7), $p27^{Kip1}$ (8–10) and $p_{57}^{KiP2}$ (11,12). The Ink group includes four members: $p16^{INK4A/MTS1/CDKN2}$ (13), $p15^{INK4B/MTS2}$ (14), $p18^{INK4C}$ (15), and $p19^{INK4D}$ (16). p27 is a negative regulator implicated in G1 phase arrest by TGFβ, cell-cell contact, agents that elevate cyclic AMP, and the growth inhibitory drug rapamycin (17–21). p27 associates with multiple G1 cyclin-dependent kinases in non-proliferating cells, abrogating their activity (4, 8–10).

To assess its role as a potential tumor suppressor, the $p27^{Kip1}$ gene was mapped to 12p12–12p13.1 and no tumor-specific genomic mutations in a large group of primary human cancers were observed (22–24). More recently, it has been reported that proteasome-mediated degradation of p27 occurs during the cell cycle and that this degradation is increased in a subset of breast and colon carcinomas of poor prognosis (25–28). The present study was undertaken in order to assess for potential alterations of p27 expression in BPH and in a well characterized cohort of patients with primary and metastatic prostatic cancer.

74 prostate carcinomas from primary and metastatic sites, representing different hormone sensitivities were analyzed. Normal prostatic tissues and cases of benign prostatic hyperplasia were also studied. In order to evaluate prostatic tissue of p27 null mice, eight 7 month old and six greater than 12 month old littermate pairs of wild-type and p27 knockout animals were used. Levels of expression and microanatomical localization of p27 protein and RNA transcripts were determined by immunohistochemistry and in situ hybridization with specific antibodies and probes, respectively. Comparative analyses between immunohistochemistry, immunoblotting and immunodepletion assays were also conducted in a subset of cases. Association between alterations in p27 expression and clinicopathological variables were evaluated using the two-tailed Fisher's exact test. Disease relapse-free survivals were evaluated using the Kaplan-Meier method and the Logrank test. Distinct anomalies in the expression of p27 in benign and malignant human prostate tissues are reported. The normal human prostate shows abundant amounts of p27 and high levels of p27 messenger in both epithelial and stroma cells. However, p27 protein and transcripts are almost undetectable in epithelial and stroma cells of BPH lesions. It is also reported that p27-null mice develop hypercellular prostatic glands which histologically resemble human BPH. Based on these findings we postulate that the loss of p27 expression in human prostate may be causally linked to BPH. Prostatic carcinomas can be categorized into two groups: those that contain detectable p27 protein and those that do not. In contrast to BPH, however, both groups of prostatic carcinomas contain abundant p27 transcripts. Moreover, primary prostatic carcinomas displaying the p27-negative phenotype appear to be biologically more aggressive, based on their association with time to prostate specific antigen (PSA) failure following radical prostatectomy. These results support the postulate that BPH is not a premalignant lesion in the pathway of prostate cancer development. Data also suggest that prostatic carcinoma develops along two different pathways, one involving the loss of p27 and the other using other processes that circumvent the growth suppressive effects of p27.

SUMMARY OF THE INVENTION

This invention provides a method for determining the aggressiveness of a prostate carcinoma comprising: (a) obtaining a sample of the prostate carcinoma; and (b) detecting the presence of p27 protein in the prostate carcinoma, the absence of p27 indicating that the prostate carcinoma is aggressive.

This invention also provides a method for diagnosing a beign prostate hyperplasia comprising: (a) obtaining an appropriate sample of the hyperplasia; and (b) detecting the presence of the p27 RNA, a decrease of the p27 RNA indicating that the hyperplasia is beign. In an embodiment, the above method further detects the protein expression of p27 wherein this additional step may be performed before or after the detection of the presence of the p27 RNA.

This invention provides a method for predicting the life-span of patient with prostate carcinoma comprising: (a) obtaining a sample of the prostate carcinoma; and (b) detecting the presence of p27 protein in the prostate carcinoma, the presence of the p27 protein indicating that the patient can live longer than the patient who are undetectable p27 protein.

This invention also provides a method for increasing the life-span of patient with prostate carcinoma comprising inducing the expression of p27 protein in the prostate carcinoma.

This invention provides a method for prolong life-span of patient with prostate carcinoma which comprises introducing a nucleic acid molecule having sequence encoding a p27 protein into the carcinoma cell under conditions permitting expression of said gene so as to prolong the life-span of the patient with said prostate carcinoma. In an embodiment, the nucleic acid molecule comprises a vector. The vector includes, but is not limited to, an adenovirus vector, adeno-associated virus vector, Epstein-Barr virus vector, Herpes virus vector, attenuated HIV virus, retrovirus vector and vaccinia virus vector.

This invention provides a method for prolong life-span of patient with prostate carcinoma which comprises introducing an effective amount of p27 protein into the carcinoma cell so as to thereby prolong the life-span of the patient with said prostate carcinoma.

This invention provides a method for prolong life-span of patient with prostate carcinoma which comprises introducing an effective amount of a substance capable of stabilizing the p27 protein into the carcinoma cell so as to thereby prolong the life-span of the patient with said prostate carcinoma.

This invention provides a composition for prolong life-span of patient with prostate carcinoma which comprises an effective amount of a nucleic acid molecule having sequence encoding a p27 protein and a suitable carrier.

This invention provides a composition for prolong life-span of patient with prostate carcinoma which comprises an effective amount of the p27 protein and a suitable carrier.

This invention provides a composition for prolong life-span of patient with prostate carcinoma which comprises an effective amount a substance capable of stabilizing the p27 protein and a suitable carrier.

BRIEF DESCRIPTION OF THE FIGURES

Figures for the First Series of Experiments

FIGS. 1A–1H

Figure 1H:
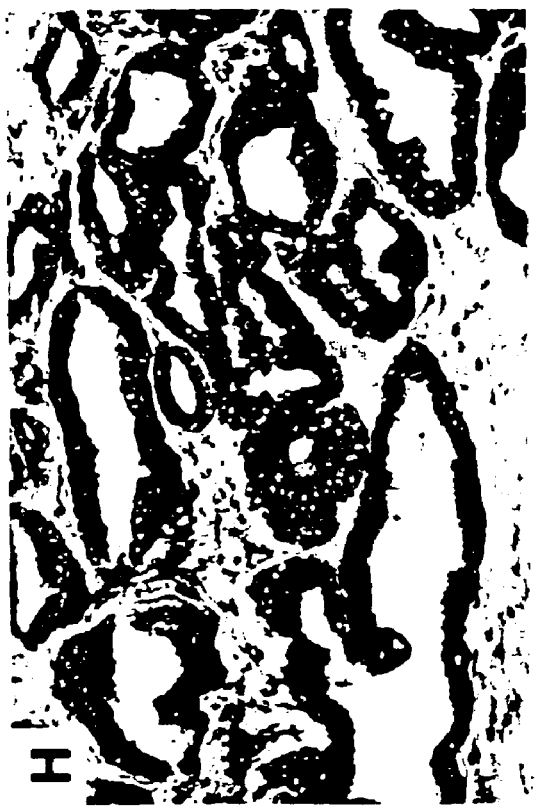

Histological analysis, immunohistochemistry, and in situ hybridization of human primary and metastatic prostatic carcinomas. (1A–1C) Photomicrographs of primary prostatic carcinomas processed as follows: (1A) Immunohistochemical staining against p27 of a prostatic intra-epithelial neoplastic (PIN) lesion; note the intense positive immunoreactivities observed in the nuclei of the tumor cells growing into the lumen. (1B) Immunohistochemical staining against p27 of another PIN lesion showing dysplastic changes; note the intense positive immunostaining in the nuclei of normal epithelial cell and the low-to-undetectable staining of the tumor cells dissecting the gland and growing into the lumen. (1C) Undetectable levels of p27 protein in an invasive primary prostatic carcinoma; note the staining of a normal gland trapped into the tumor. (1D–1F) Photomicrographs of metastatic prostatic carcinomas processed as follows: (1D) Immunohistochemical staining against p27 of a metastatic prostate carcinoma to lymph node; note the intense nuclear staining of both tumor cells and lymphocytes (cells in the germinal center display low p27 levels). (1E) Immunohistochemical staining against p27 of another metastatic prostate carcinoma to lymph node; note the intense positive immunostaining in the nuclei of lymphocytes and the undetectable levels of p27 staining on the tumor cells. (1F) Immunohistochemical staining against p27 of a metastatic prostate carcinoma to bone; note the positive immunoreactivities in the nuclei of osteoblasts and the lack of staining of tumor cells. (1F–1G) Photomicrographs of a primary invasive prostatic carcinoma processed as follows: (1F) Low-to undetectable immunohistochemical staining against p27 in the tumor cells; note the staining of a normal gland trapped into the tumor. (1G) In situ hybridization on a consecutive section from the case illustrated in panel (1H) showing high mRNA levels of p27$^{Kip1}$ even in p27-negative tumor cells utilizing the anti-sense probe to p27$^{Kip1}$. Original magnification (1A) trough (1H) 400×.

FIGS. 2A–2D

In certain prostatic carcinomas p27 protein is a functional cyclin-dependent kinase inhibitor. (2A) Immunohistochemical staining correlates with the presence of p27 by immunoblotting. Tumors #1 and #2 were negative and tumor #3 positive for p27 protein expression, paralleling their IHC patterns. (2B) Immunodepletion of p27 extracts. Extracts obtained from tumors #2 and #3 were subjected to sequential depletion with antibodies specific to p27 or a non-specific rabbit anti-mouse (RaM). Following depletion, the proteins in the supernatants were resolved and the presence of p27 determined by immunoblotting. (2C) Depletion of p27 depletes heat stable cyclin-dependent kinase inhibitory activity. The supernatant shown in panel B was boiled and following clarification the soluble fraction was incubated with different amounts of recombinant cyclin E/CDK2 kinase and the degree of inhibition of cylin E/CDK2 activity on histone H1 substrate was measured. (2D) The amount of each kinase used is shown in the panel and the bars are representative activities on an arbitrary scale. Depletion with either RaM or p27 specific antibodies did not affect the inhibitory activity of the p27 negative tumor; however, depletion of p27 from the positive tumor extract completely ablated the heat stable inhibitor activity.

FIG. 3

Recurrence-free proportion analysis of patients with primary prostate carcinoma (n=42) as assessed by time to detectable PSA. Patients who had PSA relapse were classified as failures, and patients with PSA relapse, or those who were still alive or died from other disease or lost to follow-up during the study period, were coded as censored. Time to relapse was defined as the time from date of surgery to the endpoint (relapse or censoring). Disease relapse-free survivals were evaluated using the Kaplan-Meier method and the Logrank test. A trend was observed between a p27 negative phenotype and early relapse (p=0.08).

FIGS. 4A–4F

Histological analysis, immunohistochemistry, and in situ hybridization of human normal prostate and benign prostatic hyperplasia. (4A–4C) Photomicrographs of consecutive sections of normal prostate tissue processed as follows: (4A) Immunohistochemical staining against p27; intense positive immunoreactivities are observed in the nuclei of epithelial cells in the luminal side of the acinus, with decreased reactivities in the nuclei of basal and stroma cells. (4B) In situ hybridization showing high mRNA levels of p27$^{Kip1}$ in both epithelial and stroma cells utilizing the anti-sense probe. (4C) In situ hybridization utilizing the sense probe to p27$^{Kip1}$ showing lack of signals in both epithelial and stroma cells. (4D–4F) Photomicrographs of consecutive tissue sections of a benign prostatic hyperplastic nodule processed as follows: (4D) Immunohistochemical staining against p27; note the lack or almost undetectable levels of immunoreactivity observed in the nuclei of both epithelial and stroma cells in the luminal side of the acinus, with decreased reactivities in the nuclei of basal and stroma cells. (4E) In situ hybridization showing low-to-undetectable p27$^{Kip1}$ transcripts also in both epithelial and stroma cells utilizing the anti-sense probe; note the strong signal of the cellular inflammatory infiltrates that serve as an internal positive control. (4F) In situ hybridization utilizing the sense probe to p27$^{Kip1}$ showing lack of signals in epithelial and stroma cells, as well as cellular inflammatory elements. Original magnifications: (4A), (4B) and (4C) 1000×; (4D), (4E) and (4F) 400×.

FIGS. 5A–5D

Histopathological analysis of the prostatic tissues of 12 month old p27+/+ (5A) and p27−/− (5B–5D) mice. Photomicrographs of tissue sections of normal prostate samples processed as follows: (5A) Hematoxylin and eosin staining of a prostate gland of a p27+/+ mouse showing well defined acini of epithelial cells surrounded by a stroma containing few fibroblasts and poor in supportive connective tissue components. (5B) Hematoxylin and eosin staining of a prostate gland of a p27−/− mouse showing multiple and complex glands and hypercellular acini of epithelial cells surrounded by fibromuscular stroma cells in a connective tissue displaying abundant supportive components. (5C and 5D) Hematoxylin and eosin stainings of a prostate gland of a p27−/− mouse, high power details, illustrating the complexity of the glands and abundant fibromuscular stroma elements (5C), as well as the hypercellularity of the acini (5D). Original magnifications: (5A) and (5B) 200×; (5C) and (5D) 400×.

Figures for the Second Series of Experiments

Figure 6A:
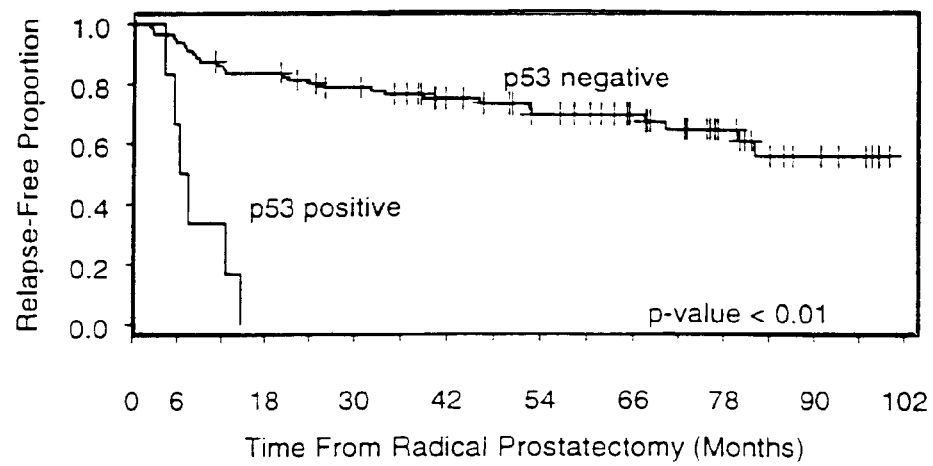
Figure 6B:
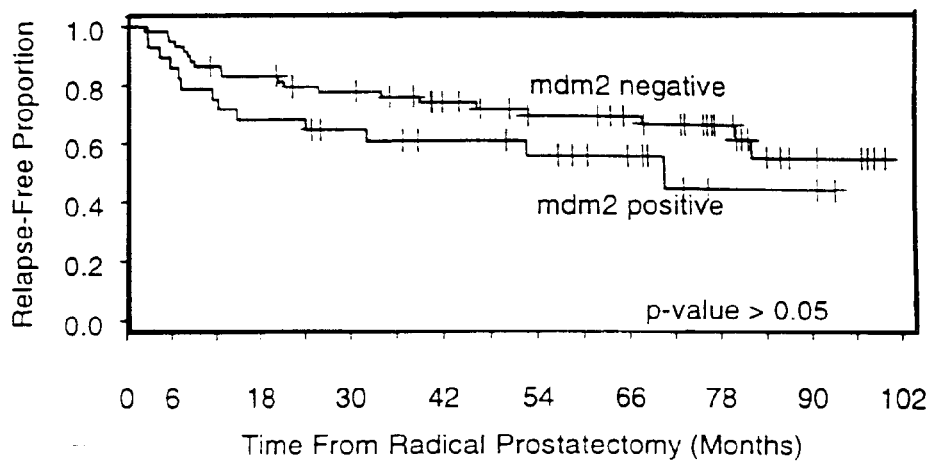
Figure 6C:
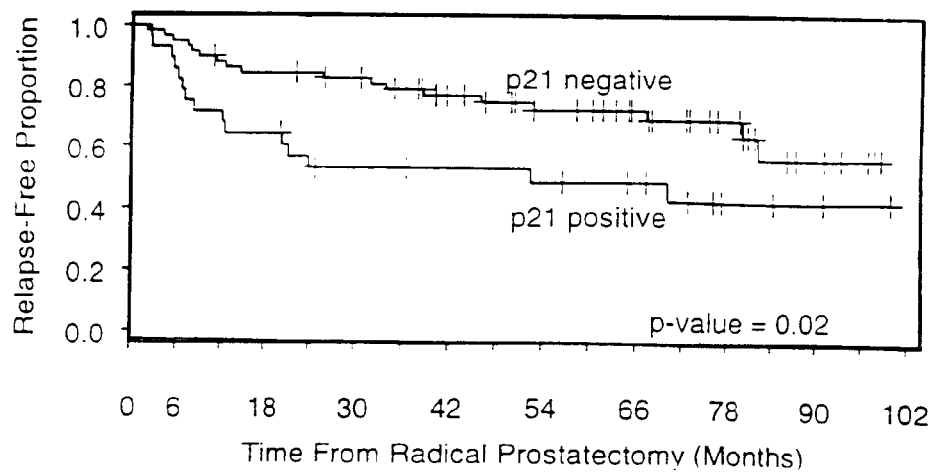

FIGS. 6A–6C Progression-free and survival curves for patients with primary prostate cancer. The Kaplan-Meier method was used to estimate overall disease free survival. The log-rank analysis was used to compare the different curves. (6A) progression was significantly reduced in patients with tumors displaying a p53-postive phenotype (P<0.01). (6B), progression was not related to mdm2 status. (6C), progression was significantly reduced in patients with tumors displaying a p21 positive phenotype (P=0.0165).

Figure 7A:
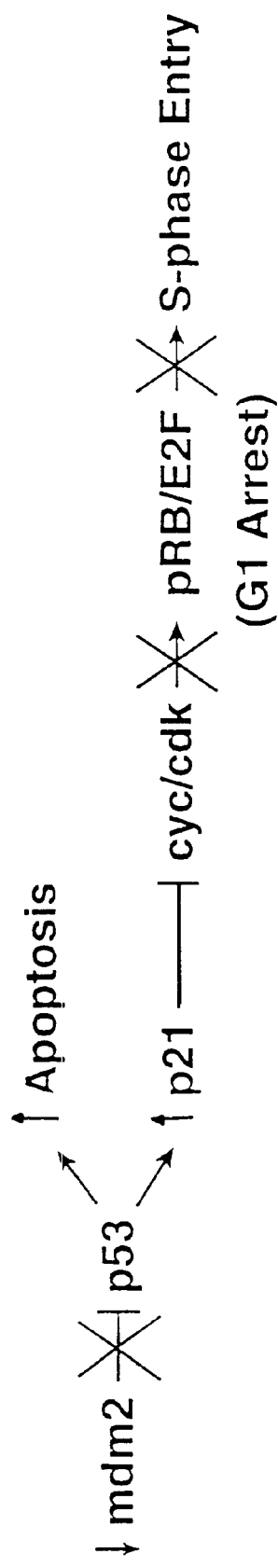
Figure 7B:
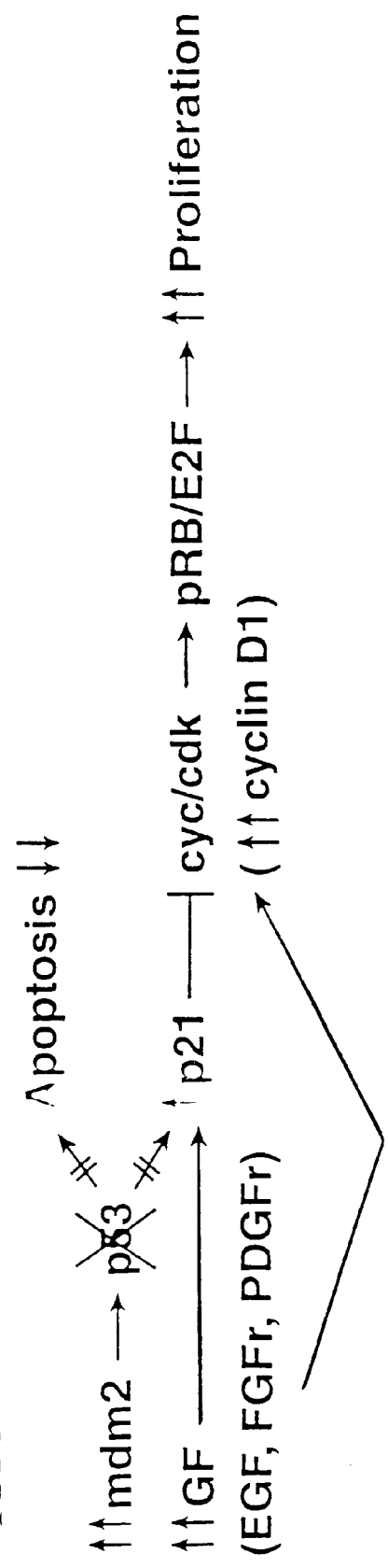

FIGS. 7A–7B Diagrammatic representation of the p53-pathway (7A), and alterations that may develop during tumor progression in prostate cancer (7B). (7A) p53 regulates the expression of several genes involved in cell cycle arrest (ie, p21) and apoptosis (ie, bax). p21 binds to heterodimeric protein kinases formed by cyclins and cyclin-dependent kinases (Cdk's), blocking phosphorylation of pRB/E2F1 complexes and abrogating S-phase entry. p53 also produces an autoregulatory feed back loop by transactivating mdm2. (7B) Overexpression of mdm2 has been observed to occur in several tumor types, and it is considered an oncogenic event. Upon binding to mdm2, p53 products are trasncriptionally inactivated and triggered for degradation. This will release the G1 arrest imposed, in part, by p21 and abolish the apoptotic signals of the pathway. Thus, inactivation of p53 will favor proliferative activity, immortality, and development/accumulation of further DNA damage or mutations. The increased p21 expression observed in our study could be produced via growth factor signaling, which would also impact on cyclin D1 expression. The increment of p21 does not appear to be able to control the proliferative activity of tumor cells, as attested by the association of p21 positive phenotype and high Ki67 proliferative index. Taken together, mdm2 overexpression will inactivate the p53-pathway, while increased mitogenic activity will offset the RB-pathway. The mechanistic basis for this dual requirement stems, in part, from the deactivation of a p53-dependent cell suicide program that would normally be brought about as a response to uncheked cellular proliferation resulting from RB-deficiency.

Figures for the Fourth Series of Experiments

FIGS. 8A–8B Immunohistochemistry and in situ hybridization of human benign prostatic hyperplasia (BPH). Consecutive sections of benign hyperplastic prostate tissue were processed as follows: (8A) Immunohistochemical staining of p16 is shown. Protein expression levels are undetectable in both epithelial and stromal components. (8B) In situ hybridization shows undetectable mRNA levels of p16 in both epithelial and stromal components when the antisense probe is used.

FIGS. 9A–9D Immunohistochemistry and in situ hybridization of human primary prostatic carcinomas. Consecutive sections of primary human prostate cancer tissue were processed as follows: (9A) Immunohistochemical staining of p16 is shown. Lack of immunoreaction noted in the nuclei and cytoplasm of both epithelial and stromal components. (9B) In situ hybridization reveals undetectable mRNA levels of p16 in both epithelial and stromal components when the antisense probe is used. (9C–9D) Histologic analysis, immunohistochemistry, and in situ hybridization of human primary prostatic carcinoma showing p16 overexpression. Consecutive sections of primary human prostate cancer tissue were processed as follows: (9C) Immunohistochemical staining of p16 is shown. Note strong brown immunoreaction observed in the nuclei of cells. Faint cytoplasmic staining is noted as well. (9D) In situ hybridization shows high mRNA levels of p16 in epithelial cells when the antisense probe is used. A normal gland (see pointer) serves as an internal negative control in both the immunohistochemical analysis in FIG. 9C and also the in situ hybridization analysis in FIG. 9D.

Figure 10:
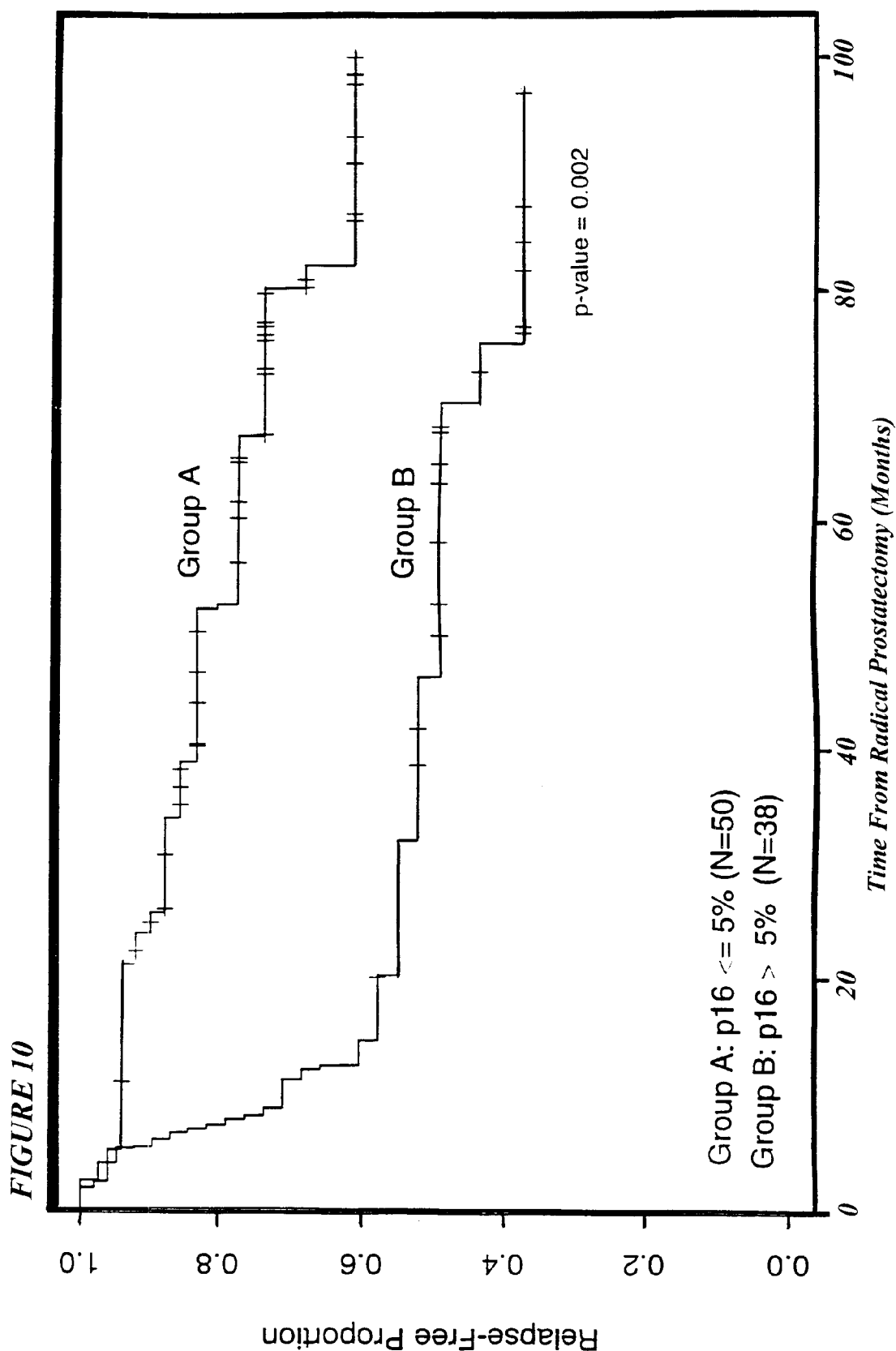

FIG. 10 Kaplan-Meier curves, using the log rank test, stratified by p16 groups (group A or group B) of patients with primary prostate carcinoma (n=88) as assessed by time to detectable PSA level post prostatectomy. Time to relapse was defined as the time from the date of surgery to the time of PSA elevation after surgery. The median time to relapse for group A has not been reached. The median time to relapse for group B was 46.25 months. Patients who had PSA relapse were classified as having treatment failures and tumor recurrence.

DETAILED DESCRIPTION OF THE INVENTION

This invention provides a method for determining the aggressiveness of a prostate carcinoma comprising: (a) obtaining a sample of the prostate carcinoma; and (b) detecting the presence of p27 protein in the prostate carcinoma, the absence of p27 indicating that the prostate carcinoma is aggressive.

This invention also provides a method for diagnosing a beign prostate hyperplasia comprising: (a) obtaining an appropriate sample of the hyperplasia; and (b) detecting the presence of the p27 RNA, a decrease of the p27 RNA indicating that the hyperplasia is beign. In an embodiment, the above method further detects the protein expression of p27 wherein this additional step may be performed before or after the detection of the presence of the p27 RNA.

This invention provides a method for predicting the life-span of patient with prostate carcinoma comprising: (a) obtaining a sample of the prostate carcinoma; and (b) detecting the presence of p27 protein in the prostate carcinoma, the presence of the p27 protein indicating that the patient can live longer than the patient who are undetectable p27 protein.

This invention also provides a method for increasing the life-span of patient with prostate carcinoma comprising inducing the expression of p27 protein in the prostate carcinoma.

This invention provides a method for prolong life-span of patient with prostate carcinoma which comprises introducing a nucleic acid molecule having sequence encoding a p27 protein into the carcinoma cell under conditions permitting expression of said gene so as to prolong the life-span of the patient with said prostate carcinoma. In an embodiment, the nucleic acid molecule comprises a vector. The vector includes, but is not limited to, an adenovirus vector, adeno-associated virus vector, Epstein-Barr virus vector, Herpes virus vector, attenuated HIV virus, retrovirus vector and vaccinia virus vector.

Methods to introduce a nucleic acid molecule into cells have been well known in the art. Naked nucleic acid molecule may be introduced into the cell by direct transformation. Alternatively, the nucleic acid molecule may be embedded in liposomes. Accordingly, this invention provides the above methods wherein the nucleic acid is introduced into the cells by naked DNA technology, adenovirus vector, adeno-associated virus vector, Epstein-Barr virus vector, Herpes virus vector, attenuated HIV vector, retroviral vectors, vaccinia virus vector, liposomes, antibody-coated liposomes, mechanical or electrical means. The above recited methods are merely served as examples for feasible means of introduction of the nucleic acid into cells. Other methods known may be also be used in this invention.

This invention provides a method for prolong life-span of patient with prostate carcinoma which comprises introducing an effective amount of p27 protein into the carcinoma cell so as to thereby prolong the life-span of the patient with said prostate carcinoma.

This invention provides a method for prolong life-span of patient with prostate carcinoma which comprises introducing an effective amount of a substance capable of stabilizing the p27 protein into the carcinoma cell so as to thereby prolong the life-span of the patient with said prostate carcinoma. Such substance may be either inhibiting the protease which degrade the p27 protein or it may interact with p27 in such a way that the protein will be resistant to degradation. By administering such substance into the cell, the effective amount of p27 protein will be increased.

This invention provides a composition for prolong life-span of patient with prostate carcinoma which comprises an effective amount of a nucleic acid molecule having sequence encoding a p27 protein and a suitable carrier.

As used herein, the term "suitable carrier" encompasses any of the standard carriers. The composition may be constituted into any form suitable for the mode of administration selected. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

This invention provides a composition for prolong life-span of patient with prostate carcinoma which comprises an effective amount of the p27 protein and a suitable carrier.

This invention provides a composition for prolong life-span of patient with prostate carcinoma which comprises an effective amount a substance capable of stabilizing the p27 protein and a suitable carrier.

This invention provides a method for determining the rate of proliferation of a prostate cancer comprising: (a) obtaining a sample of the prostate cancer; and (b) detecting the presence of p21 protein in the prostate cancer, the presence of p21 indicating that the prostate cancer will have a high proliferation rate.

This invention also provides a method for determining the rate of proliferation of a prostate cancer comprising: (a) obtaining a sample of the prostate cancer; and (b) detecting the mdm2 expression in the prostate cancer, the overexpression of mdm2 indicating that the prostate cancer will have high proliferation rate.

This invention provides a method for determining whether a prostate cancer would be metastatic comprising: (a) obtaining a sample of the prostate cancer; and (b) detecting the level of cyclin D1 expression in the prostate cancer, the overexpression of cyclin D1 indicating that the prostate cancer will be metastatic. In an embodiment, the prostate cancer is metastatic to bone.

This invention provides a method for determining the tumor recurrence in prostate cancer comprising: (a) obtaining a sample of the prostate cancer; and (b) detecting the expression of the cyclin-dependent kinase inhibitor p16 in the prostate cancer, the overexpression of p16 indicating that the prostate cancer will have high tumor recurrence.

This invention will be better understood from the Experimental Details which follow. However, one skilled in the art will readily appreciate that the specific methods and results discussed are merely illustrative of the invention as described more fully in the claims which follow thereafter.

Experimental Details
Experimental Details for First Series of Experiments
Materials and Methods Patient Characteristics and Tissues. A cohort of 74 patients with prostatic carcinoma were evaluated. Tissues were obtained from the Department of Pathology, Memorial Sloan-Kettering Cancer Center, New York. Samples were formalin-fixed, paraffin-embedded tissue specimens. Fourty-two primary prostate adenocarcinoma specimens were evaluated, as well as 9 metastases to lymph node and 23 metastases to bone. Normal prostatic tissue and/or areas of benign prostatic hyperplasia adjacent to tumor were observed in the majority of the primary cases studied. These tissues were also analyzed as part of the study. In addition, 10 pairs of frozen normal and tumor prostate tissues were utilized for antibody titration, as well as comparative analyses between immunohistochemistry, immunoblotting and immunodepletion assays (see below). Representative hematoxylin-eosin stained sections were examined to evaluate the histopathological characteristics of the lesions to be analyzed, including the ratio of normal-to-tumor content for microdissection techniques.

In order to evaluate prostatic tissue of p27 null mice, eight 7 month old and six greater than 12 month old littermate pairs of wild-type and p27 knockout animals were used. Tissues were dissected, weighted and processed for histology by formalin fixation and paraffin embedding. Tissue sections were cutted and stained with hematoxylin-eosin for histologic analysis. All sections were utilized to count the number of acini per gland, a process that was conducted utilizing magnifications of 200×.

Antibodies and Immunohistochemistry. The following well characterized antibodies and corresponding final working dilutions were used for the present study: monoclonal antibody p27/Kip1 (Ab-2, Oncogene Science, Boston, Mass.—0.1 ug/ml final concentration) and anti-p27 affinity purified rabbit antiserum (1:500 dilution). A non-immune rabbit serum and mouse monoclonal antibody MIgS-KpI were used as negative controls at similar working dilutions. Deparaffinized sections were treated with 3% $H_2O_2$ in order to block endogenous peroxidase activity. Sections were subsequently immersed in boiling 0.01% citric acid (pH 6.0) in a microwave oven for 15 minutes to enhance antigen retrieval, allowed to cool, and incubated with 10% normal horse or normal goat sera to block non-specific tissue immunoreactivities. Primary antibodies were then incubated overnight at 4° C. Biotinylated horse anti-mouse IgG antibodies (Vector Laboratories, Burlingame, Calif.—1:500 dilution) or goat anti-rabbit antibodies (Vector Laboratories—1:800 dilution) were applied for 1 hour, followed by avidin-biotin peroxidase complexes for 30 minutes (Vector Laboratories—1:25 dilution). Diaminobenzidine was used as the final chromogen and hematoxylin was used as the nuclear counterstain. Nuclear immunoreactivities were classified as a continuum data (undetectable levels or 0% to homogeneous staining or 100%). Tumors were grouped into two categories defined as follows: negative (0% or undetectable staining to <20% nuclear immunoreactivity in tumor cells), and positive (neoplasms with ≧20% tumor cells with nuclear staining) (see statistical section).

Probes and In Situ Hybridization. Digoxigenin-labeled probes were used for in situ hybridization and 1 ug of recombinant plasmid pCR™ II (Invitrogen, San Diego, Calif.), containing the full length human p27 gene (gift of Dr. M. Pagano, New York University School of Medicine, NY) was linearized by BamHI and XbaI to generate antisense and sense transcripts. Riboprobes were generated with T7 and SP6 polymerase for 2 hours at 37° C. in 1× transcription buffer (Boehringer Mannheim, Indianapolis, Ind.), 20 U of RNAse inhibitor, 1 mmol/L each of ATP, GTP, CTP, 6.5 mmol/L UTP and 3.35 mmol/L digoxigenin-UTP. Deparaffinized tissue sections were rinsed in water and PBS for 10 minutes. The slides were digested with Proteinase K (50 ug/ml) for 18 minutes at 37° C. in PBS, and post-fixed at 4° C. in a freshly prepared solution of 4% paraformaldehyde in PBS for 5 minutes. Prehybridization was done for 30 minutes at 45° C. in 50% formamide and 2×SSC. The hybridization buffer consisted of 50% deionized formamide (v/v), 10% dextran sulphate (50% stock solution), 2×SSC (20× stock solution), 1% SDS (10% stock solution), and 0.25 mg/ml of herring sperm DNA (10 mg/ml). Hybridization was peformed overnight at 45° C. applying 10 pmol/L digoxigenin-labeled riboprobe in 50 ul of hybridization buffer per section under a coverslip. The coverslips were removed and the slides were washed in pre-warmed 2×SSC for 20 minutes at 60° C. twice, followed by washes in pre-warmed 0.5×SSC and 0.01×SSC at 60° C. for 20 minutes, respectively. After these washes the slides were incubated in normal sheep serum diluted in buffer pH 7.5 and successively in the same buffer with antibody anti-digoxigenin-AP (Boehringer Mannheim, Indianapolis, Ind.) at dilution of 1:1500 for 1 hour at room temperature. The visualization was accomplished by nitro-blue tetrazolium 5-bromo-4-chloro-3-indoylphosphate. The slides were counterstained with methyl green and mounted.

Immunoblotting and Immunodepletion Assays. Proteins were extracted from three OCT-embedded prostatic carcinomas and resolved on polyacrylamide gels for immunoblotting with p27-specific antibodies. Extracts obtained from p27 positive and negative tumors were subjected to sequential depletion with antibodies specific to p27 or a non-specific rabbit anti-mouse (RaM). Following depletion, the proteins in the supernatants were resolved and the presence of p27 determined by immunoblotting. Aliquots of these supernatants were briefly boiled and following clarification the soluble fraction was incubated with different amounts of recombinant cyclin E/CDK2 kinase and the degree of inhibition of cylin E/CDK2 activity on histone H1 substrate was measured.

Statistical Methods. The statistical analyses were conducted as follows. For alterations of the p27, we divided patients into two groups: p27 negative (0% or no immunohistochemical staining to <20% tumor cells displaying nuclear reactivities) or p27 positive (≧20% tumor cells with nuclear immunostaining with IHC). The data analyses were conducted to explore the relationship between p27 alterations and clinicopathological variables such as presentation (primary, lymph node metastases, and bone metastases), clinical stage (B, C, D), total Gleason score (6 or less versus 7 or more), and hormonal status (naive versus androgen-independent) in a total 74 patients. For 42 patients with primary prostate cancer who underwent radical prostatectomy, further analysis was conducted to evaluate the relationship between p27 alterations and clinical variables, including those described above and PSA relapse (yes and no). Two-tail Fisher's exact test was utilized to assess these associations and two tailed p-values were employed as a significant level (29). The FREQ procedure in SAS was used in this study (30). In the analysis of disease relapse-free survival, patients who had PSA relapse were classified as lost failures, and patients with PSA relapse, or those who were still alive or died from other disease or to follow-up during the study period, were coded as censored. Disease relapse-free survivals were evaluated using the Kaplan-Meier method (31) and the Logrank test (32). The LIFETEST procedure in SAS was used (30). Proportional hazards analysis was used to obtain maximum likelihood estimates of relative risks and their 95% confidence intervals (33, 34).

Experimental Results and Discussion

Experimental Results and Discussion for the First Series of Experiments

Figure 1G:
Figure 2A:
Figure 2B:
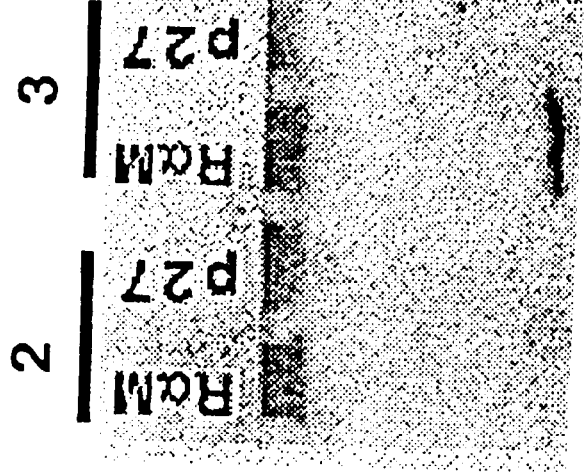
Figure 2C:
Figure 2D:
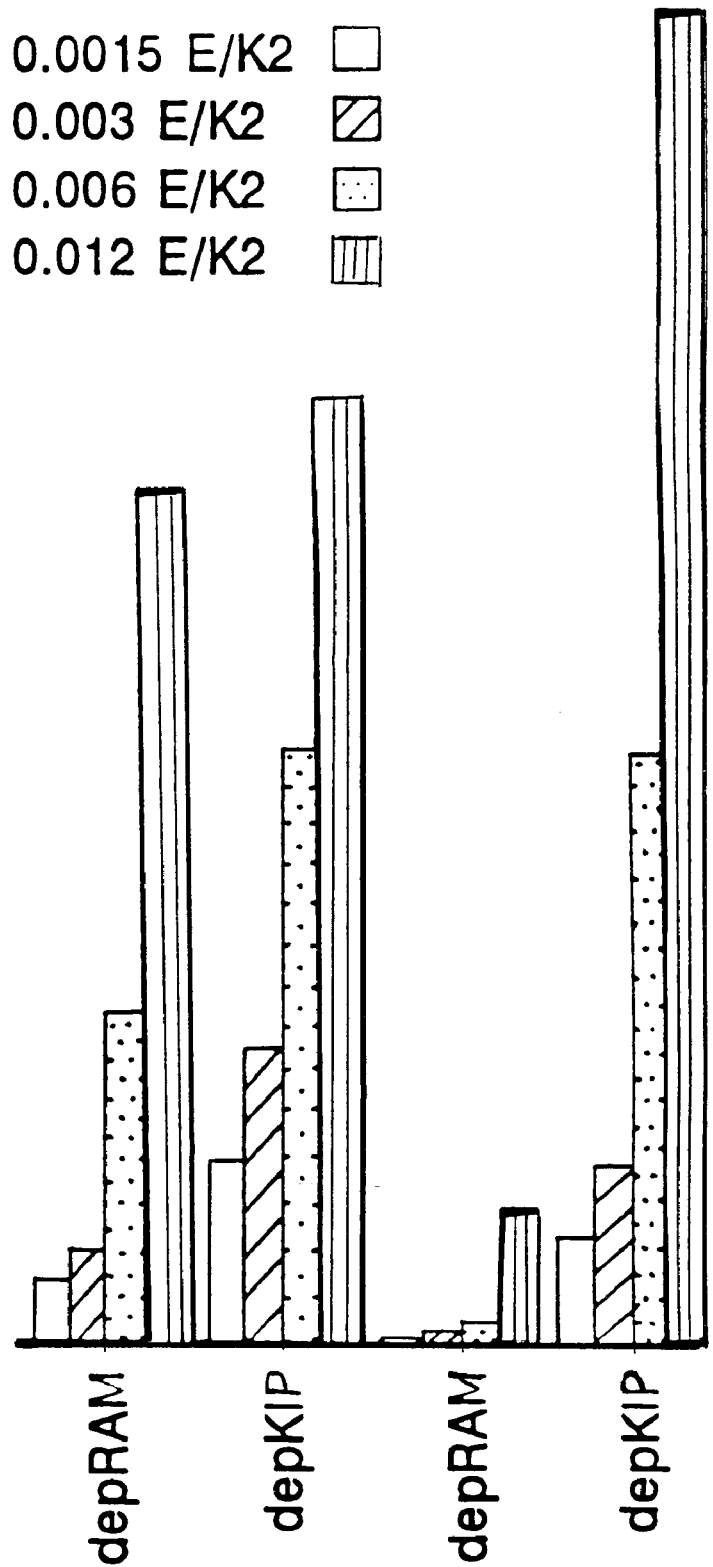

To determine whether loss of p27 expression was a common feature in prostate cancer, we analyzed 74 prostate carcinomas from primary and metastatic sites, representing different hormone sensitivities. Included were 42 hormone-naive primary tumors, some with associated prostatic intraepithelial neoplastic (PIN) lesions, and 32 metastatic carcinomas from lymph node tumors (n=9) and bone metastases (n=23). Thirteen of these metastatic lesions were from hormone-naive cases, while the remaining 19 metastases were obtained after hormonal treatment. PIN lesions displaying a cribiform or pseudopapillary pattern expressed high levels of p27 protein (FIG. 1A) and were associated with p27-positive invasive prostatic carcinomas. In contrast, PIN lesions displaying a flat growth pattern had low to undetectable p27 levels (FIG. 1B) and were associated with p27-negative invasive tumors. Of the invasive primary prostatic carcinomas studied, 12 of 42 (28.5%) cases had an intense nuclear immunoreactive p27 pattern in the malignant cells (data not shown). The remaining 30 (71.5%) primary neoplasms displayed altered patterns of expression: 12 cases had undetectable p27 levels (FIG. 1C), while 18 cases had a heterogeneous pattern of expression (data not shown). In metastatic lesions, 7 of 32 (21.9%) showed intense p27 nuclear immunostaining in most tumor cells (FIG. 1D). The remaining 25 (78.1%) metastatic lesions had either heterogeneous (data not shown) or undetectable nuclear expression of p27 (FIGS. 1E and 1F). Interestingly, all but one of the nine patients with hormone-independent bone lesions displayed altered p27 expression. Four of these 9 cases had undetectable p27 protein expression (FIG. 1F), 4 cases had heterogeneous patterns of p27 expression ranging from 30% to 40% tumor cells with weak positive staining, and one case displayed 80% positive tumor cells. However, high levels of $p27^{Kip1}$ mRNA, as determined by in situ hybridization to a p27 cDNA probe, were found in all tumors even when the lesions displayed undetectable levels of p27 protein (FIGS. 1G and 1H).

In the group of tumors that expressed p27, we next determined if the p27 protein was inactivated. To accomplish this we extracted protein from fresh frozen samples and measured the heat stable Cdk inhibitory activity, using cyclin E/CDK2 as a substrate, remaining in extracts following depletion with p27-specific antibodies as described previously (17) (FIG. 2). Depletion of p27 protein was confirmed by immunoblotting. As expected, the depletion of extracts derived from p27 negative tumors did not affect the heat stable inhibitory activity, nor did depletion of p27 positive tumor extract with a non-specific rabbit-anti-mouse immunoglobulin. However, depletion of extracts derived from p27 positive tumors with the p27-specific antibody completely removed the inhibitory activity, indicating that p27 was functional as a Cdk inhibitor in these samples.

Figure 3:
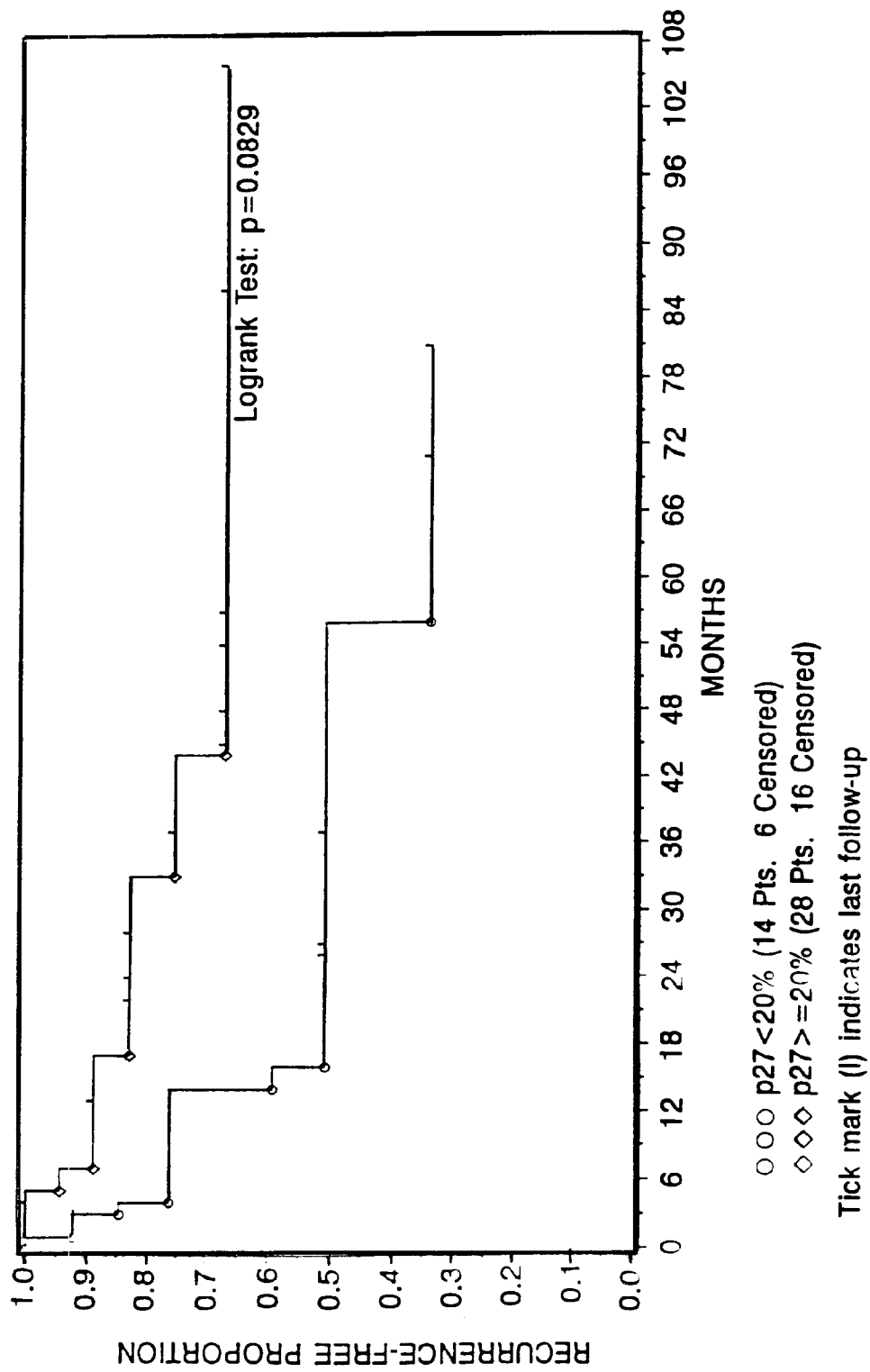

Taken together, these data suggest that prostatic carcinomas develop along two different pathways, one involving the loss of p27 and the other using alternative processes that may circumvent the growth suppressive effects of p27. In order to determine if these distinct pathways of prostate tumorigenesis correlate with clinical parameters, as reported for other tumor types (25–28), associations between p27 immunostaining, stage, total Gleason score, and hormonal status of the tumor were assessed. No associations between detectable versus undetectable p27 protein, Gleason score (6 or less versus 7 or more), or hormonal status (naïve versus androgen-independent) were observed. To assess disease aggressiveness, we evaluated the time to PSA failure, the most sensitive indicator of success or failure following radical prostatectomy, in patients treated for localized disease. Only patients who had an undetectable PSA level after surgery, an indication that the resection was complete, were considered. A trend toward an association was observed between a p27 negative phenotype and early relapse (p=0.08) (FIG. 3). This difference did not reach statistical significance due to the limited sample size of the cohort analyzed. Supporting this concept is the fact that in a multivariate proportional hazards analysis, after controlling for stage and Gleason score, p27 status still was the strongest factor in predicting PSA relapse (p=0.07).

Figures 4A, 4B, 4C, 4D, 4E, 4F:
Figure 5A:
Figure 5B:
Figure 5C:
Figure 5D:
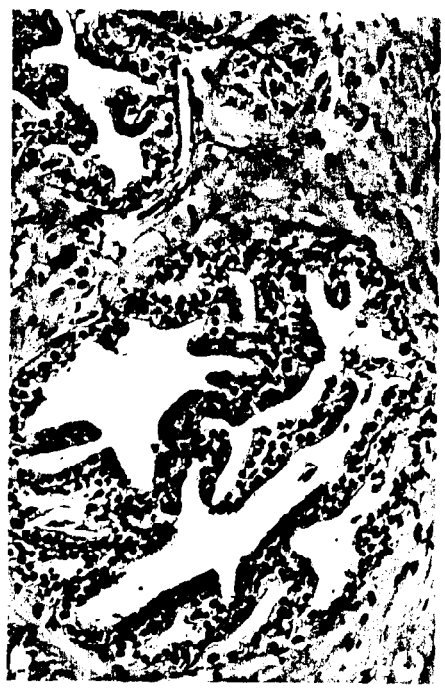

These data suggest extending the characterization of p27 expression to normal prostate and benign prostatic hyperplasia. In the normal human prostate, abundant amounts of p27 protein were detected in the ductal and acinar cells, mainly luminal elements, as well as stroma cells using immunohistochemistry. Epithelial cells displayed a strong nuclear immunostaining signal (FIG. 4A). Likewise, both epithelial and stroma cells expressed abundant p27 transcripts (FIGS. 4B and 4C), as detected by in situ hybridization. Strikingly, in 12 cases of BPH p27 expression was low to undetectable in epithelial and stroma cells in the hyperplastic nodules. Immunohistochemical staining revealed low to undetectable immunoreactivities in both epithelial and fibromuscular cells in the hyperplastic nodules (FIG. 4D). This contrasts with the strong p27 nuclear immunostaining phenotype observed in the normal prostate. Likewise, p27 mRNA transcript levels were low to undetectable on consecutive sections of BPH by in situ hybridization (FIG. 4E and 4F). In some of these BPH tissue samples we found areas of basal cell hyperplasia. These cellular elements also had low to undetectable amounts of p27 protein and transcripts (data not shown). Nevertheless, in the non-hyperplastic regions of these same BPH samples, normal ductal and acinar epithelial cells, as well as stroma elements, showed high levels of p27 expression. These results indicate that in the development of BPH, p27 transcription may be down-regulated. This finding was quite unexpected as this gene product is generally regulated at post-transcriptional levels (35–37), although members of the nuclear hormone receptor superfamily are suggested to regulate $p27^{Kip1}$ mRNA levels (38).

The targeted deletion of the p27 locus in a murine model was recently reported (39–41). p27 deficient mice are viable and display organomegaly, increased body size and female infertility. These anomalies could not be attributed to a defect of the growth hormone/IGF-1 axis, rather, they resulted from excess proliferation prior to withdrawal of cells into a terminally differentiated state (39). No increased incidence of spontaneous tumors was observed; however, many p27-null mice developed a pituitary hyperplasia reminiscent of adenoma in the intermediate lobe. These data suggest that p27 deficiency leads to hyperplasia in many tissues and organs. The high frequency of benign prostatic hyperplasia (BPH) in men and the alterations on p27 expression in that condition suggested a parallel to p27 deficiency. Previous reports of histopathological analyses of p27 null mice did not include the prostate (39–41). We next set up to determine the morphologic characteristics of the prostate gland in p27 deficient animals. Comparing the total mean prostate weights of 7 month old age-matched p27+/+ (n=8) and p27−/− (n=8) mice, the differences were not significant [mean+/−SD: 80.6 mg (+/−8.6 mg) and 90.1 mg (+/−13.3 mg), respectively (p=0.1)]. However, the mean acini counts of the total gland in these groups were significantly different [mean+/−SD: 50.4 (+/−8.5) and 74.9 (+/−8.9), respectively (p<0.01)]. A similar relationship was observed in the mean total prostate weights of the old (greater than 12 months) p27+/+ (n=6) and p27−/− (n=6) mice [mean+/−SD: 114.0 mg (+/−18.5 mg) and 119.0 mg (+/−26.8 mg), respectively (p=0.7)], and the mean acini counts [mean+/−SD: 54.7 (+/−6.5) and 73.8 (+/−5.3), respectively (p<0.01)]. The significant increase in the number of acini in both young and old p27 deficient mice was associated with histopathological differences that became more accentuated in the elderly group. The hyperplastic prostate of the older p27−/− mice showed enlarged glands, development of hypercellular acini of epithelial cells, and an increase in fibromuscular stroma cells (FIG. 5). These histological changes are reminiscent of BPH in humans and support the hypothesis that the loss of p27 expression in human prostate may be causally linked to BPH.

It has been suggested that BPH and malignant prostate growth share a common pathway because they commonly coexist and demonstrate androgen dependency (42–44). However, this relationship remains unclear since BPH tends to develop in the transition zone, while the majority of carcinomas develop in the peripheral zone (45–48). Results from the present study reveal that, unlike in the BPH lesions, prostatic carcinoma cells regulate p27 expression at the post-transcriptional level. Taken together these data support the postulate that BPH is not a premalignant lesion in prostate cancer development.

Coordinate inactivation of the pathways involving the p53 and RB genes appears to be an essential requirement for the genesis of most human cancers. However, both p53 mutations and RB alterations are reported to be late and uncommon events in prostate tumor progression (49–52). Contrary to these results, data from this study indicate that inactivation of p27 is a frequent and early event in some prostate cancers. It is thus our working hypothesis that p27 represents another pathway of tumor suppression in certain human tumors, prostate cancer being a paradigm in which this concept could be further tested.

In summary, data from this study suggest that $p27^{Kip1}$ gene ablation in the mouse causes a pronounced prostatic hyperplasia, and that the loss of p27 expression in human prostate may be causally linked to BPH. In addition, data from this study suggest that prostatic carcinoma develops along two different pathways, one involving the loss of p27 and the other using alternative processes that circumvent the growth suppressive effects of p27. These phenotypes can be identified as early as in the PIN stage. Moreover, primary prostatic carcinomas displaying the p27-negative phenotype appear to be biologically more aggressive, based on their association with time to PSA failure following radical prostatectomy while controlling for other variables. The consistent alteration of p27 expression observed in all androgen-independent metastatic lesions suggests an association with tumor progression, which may be the result of the metastatic process itself. Alternatively, it may be postulated that p27 positive tumors are more sensitive to androgen ablation, the primary treatment of metastatic disease. Finally, two dissimilar mechanisms appear to be involved in the loss of p27 expression in BPH versus a subset of prostatic carcinomas. $p27^{Kip1}$ mRNA levels are extensively reduced in BPH, whereas p27 proteins are diminished to undetectable levels in some prostatic carcinomas despite detectable p27 mRNA as the result of a post-transcriptional event. These results support the postulate that BPH is not a premalignant lesion in the pathway of prostate cancer development.

References for the First Series of Experiments

1. Hartwell, L. H. & Kastan, M. B. (1994) *Science* 266, 1821–1828.
2. Cordon-Cardo, C. (1995) *Am. J. Path.* 147, 545–560.
3. Sherr, C. J. (1996) *Science* 274, 1672–1677.
4. Sherr, C. J. & and Roberts, J. M. (1995) *Genes Dev* 9, 1149–1163.
5. Harper, J. W., Adami, G. R., Wei, N., Keyomarsi, K. & Elledge, S. J. (1993) *Cell* 75, 805–816.
6. El-Deiry, W. S., Tokino, T., Velculescu, V. E., Levy, D. B., Parsons, R., Trent, J. M., Lin, D., Mercer, W. E., Kinzler, K. W. & Vogelstein, B. (1993) *Cell* 75, 817–825.
7. Xiong, Y., Hannon, G. J., Zhang, H. Casso, D., Kobayashi, R. & Beach, D. (1993) *Nature* 366, 701–704.
8. Polyak, K., Kato, J-Y., Solomon, M. J., Sherr, C. J., Mssague, J., Roberts, J. M. & Koff, A. (1994) *Genes Dev* 8, 9–22.
9. Polyak, K., Lee, M-H., Erdjument-Bromage, H., Koff, A., Roberts, J. M., Tempst, P. & Massague, J. (1994) *Cell* 78, 59–66.
10. Toyoshima, H. & Hunter, T. (1994) *Cell* 78, 67–74.
11. Lee, M-H., Reynisdóttir, I. and Massague, J. (1995) *Genes Dev.* 9, 639–649.
12. Matsuoka, M., Edwards, M. C., Bai., C., Parker, S., Zhang, P., Baldini, A., Harper, W. & Elledge, S. J. (1995) *Genes Dev.,* 9, 650–662.
13. Serrano, M., Hannon, G. J. & Beach, D. (1993) *Nature* 366, 704–707.
14. Hannon, G. J. & Beach, D. (1994) *Nature* 371, 257–261.
15. Guan, K-L., Jenkins, C. W., Li, Y., Nichols, M. A., Wu, X., O'Keefe, C. L., Matera, A. G. & Xiong, Y. (1994) *Genes Dev* 8, 2939–2952.
16. Chan, F. K. M., Zhang, J., Cheng, L., Shapiro, D. N. & Winoto, A. (1995) *Mol. Cell Biol.* 15, 2682–2688.
17. Polyak, K., Kato, J-Y., Solomon, M. J., Sherr, C. J., Massague, J., Roberts, J. M. & Koff, A. (1994) *Genes Dev* 8, 9–22.
18. Kato, J. Y., Matsuoka, M., Polyak, K., Massague, J. & Sherr, C. J. (1994) *Cell* 79, 487–496.
19. Coats, S., Flanagan, W. M., Nourse, J. & Roberts, J. M. (1996) *Science* 272, 877–880.
20. Luo, Y., Marx, S. O., Kiyokawa, H., Koff, A., Massague, J. & Marks, A. R. (1996) *Mol Cell Biol* 16, 6744–6751.
21. Millard, S. S., Yan, J., Nguyen, J., Pagano, M., Kiyokawa, H. & Koff, A. (1997) *J Biol Chem* 272, 7093–7098.
22. Ponce-Castaneda, M. V., Lee, M-H., Latres, E., Polyak, K., Lacombe, L., Montgomery, K., Mathew, S., Krauter, K., Sheinfeld, J., Massague, J. & Cordon-Cardo, C. (1995) *Cancer Res* 55, 1211–1214.
23. Pietenpol, J. A., Bohlander, S. K., Sato, Y., Rowley, J. D., Papadopoulos, N., Liu, B., Friedman, C., Trask, B. J., Roberts, J. M., Kinzler, K. W., Vogelstein, B. (1995) *Cancer Res* 55, 1206–1210.
24. Bullrich, F., MacLachlan, T. K., Sang, N., Druck, T., Veronese, M. L., Allen, S. L., Chiorazzi, N., Koff A., Huebner, K., Croce, C. M. & Giordano, A. (1995) *Cancer Res* 55, 1199–1205.
25. Loda, M., Cukor, B., Tam, S. W., Lavin, P., Fiorentino, M., Draetta, G. F., Jessup, J. M., & Pagano, M. (1997) *Nature Med.* 3, 231–234.
26. Porter, P. L., Malone, K. E., Heagerty, P. J., Alexander, G. M., Gatti, L. A., Firpo, E. J., Daling, J. R. & Roberts, J. M. (1997) *Nature Med.* 3, 222–225.
27. Catzavelos, C., Bhattacharya, N., Ung, Y. C., Wilson, J. A., Roncari, L., Sandhu, C., Shaw, P., Yeger, H., Morava-Protzner, I., Kapusta, L., Frannssen, E., Pritchard, K. I. & Slingerland, J. M. (1997) *Nature Med.* 3, 227–230.
28. Tan, P., Cady, B., Wanner, M., Worland, P., Cukor, B., Magi-Galluzzi, C., Lavin, P., Draetta, G., Pagano, M. & Loda, M. (1997) *Cancer Res.* 57, 1259–1263.
29. Mehta C. R. & Patel, N. R. (1983) *J Am Stat Assoc* 78, 427–434.
30. SAS Institute Inc, SAS/STAT User Guide, version 6 (1990).
31. Kaplan, E. L & Meier, P. (1958) *J Am Stat Assoc* 53, 457–481.
32. Peto, R., Pike, M. C., Armitage, P. Breslow, N. E., Cox, D. R., Howard, S. V., Mantel, N., McPherson, K., Peto, J. & Smith, P. G. (1977) *Br J Cancer* 35, 1–39.
33. Cox, D. R., (1972) *J R Statist Soc* 34, 187–220.
34. Cox, D. R. (1975) *Biometrika* 62, 269–279.
35. Pagano, M., Tam, S. W., Theodoras, A. M., Beer-Romero, P., Del Sal, G., Chau, V., Yew, P. R., Draetta, G. F. & Rolfe, M. (1995) *Science* 269, 682–685.
36. King, R. W., Deshaies, R. J., Peters, J-M. & Kirschner, M., (1996) *Science* 274, 1652–1659.
37. Hengst, L. & Sherr, S. I. (1996) *Science* 271, 1861–1864.
38. Liu, M., Lee, M. H., Cohen, M., Bommakanti, M. & Freedman, L. P. (1996) *Genes & Dev* 10, 142–153.
39. Kiyokawa, H., Kineman, R. D., Manova-Todorova, K. O, Soares, V. C., Hoffman, E. S., Ono, M., Khanam, D., Hayday, A. C., Frohman, L. A. & Koff, A. (1996) *Cell* 85, 721–732.
40. Nakayama, K., Ishida, N., Shirane, M., Inomata, A., Inoue, T., Shishido, N., Horii, I., Loh, D. Y. & Nakayama, K-I. (1996) *Cell* 85, 707–720.
41. Fero, M. L., Rivkin, M., Tasch, M., Porter, P., Carow, C. E., Firpo, E., Polyak, K., Tsai, L-H., Broudy, V., Perlmutter, R. M., Kaushansky, K. & Roberts, J. M. (1996) *Cell* 85, 733–744.
42. Scher, H., Steinieck, G. & Kelly, W. K. (1995) *Urology* 46, 142–148.
43. Oesterling, J. E. (1996) *Prostate (Suppl)* 6, 67–73.
44. Linehan, W., Cordon-Cardo, C., Isaacs, W., Eds. DeVita, V. T., Hellman, S, Rosenberg, S. A. (J. B. Lippincott Company, Philadelphia, 1997).
45. Bostwick, D. G. (1996) *Cancer* 78, 330–336.
46. Parkinson, M. C. (1995) *Histopathol* 27, 301–307.
47. Bostwick, D., Pacelli, A., Lopez-Beltran, A. (1996) *Prostate* 29, 117–134.

48. Lipski, B. A., Garcia, R. L. & Brawer, M. K. (1996) *Semin Urol Oncol* 14, 149–155.
49. Aprikian, A. G., Sarkis, A. S., Fair, W. R., Zhang, Z-F., Fuks, Z. & Cordon-Cardo, C. (1994) *J Urol* 151, 1276–1280.
50. Brooks, J. D., Bova, G. S., Marshall, F. F. & Isaacs, W. B. (1993) *J Urol* 150, 1278–1283.
51. Dinjens, W. N., van der Weiden, M. M., Schroeder, F. H., Bosman., F. T. & Trapman, J. (1994) *Int J Cancer* 56, 630–633.
52. Grignon, D. J., Caplan, R., Sarkar, F. H., Lawton, C. A., Hammond, E. H., Pilepich M V, Forman J D, Mesic J, Fu K K, Abrams R A, Pajak T F, Shipley W U & Cox J D. (1997) *J Natl Cancer Inst* 89, 158–165.

Second Series of Experiments

To determine the potential role of p53 inactivation in prostate cancer, we studied a well characterized cohort of 86 patients treated with radical prostatectomy. We analyzed patterns of p53, mdm2, and p21/WAF1 expression by immunohistochemistry. Results were then correlated with clinicopathological parameters of poor outcome, including time to PSA relapse. In addition, data were also correlated with proliferative index, as assessed by Ki67 antigen detection. p53 positive phenotype, defined as identification of nuclear immunoreactivity in >20% tumor cells, was observed in 6 of 86 cases (7%). An association was observed between p53 positive phenotype and decreased time to PSA relapse (P<0.01). mdm2 positive phenotype, defined as ≧20% tumor cells displaying nuclear immunoreactivity, was observed in 28 of 86 cases (32.5%). mdm2 positive phenotype was found to be associated with advanced stage (P=0.009). p21 positive phenotype, defined as >5% tumor cells with nuclear immunoreactivity, was observed in 28 of 86 cases (32.5%). An association was observed between p21 positive phenotype and high Ki67 proliferative index (P=0.002). Patients with p21 positive phenotype had a significant association with decreased time to PSA relapse (P=0.0165). In addition, a significant association was found between p21 positive phenotype and co-expression of mdm2 (P<0.01). Fourty-three of 86 cases (50%) were found to have one or more alterations, and patients with any alteration were found to have a higher rate of PSA relapse (P<0.01). It is our hypothesis that a pathway of prostate cancer progression involves p53 inactivation caused by mdm2 overexpression, and that p21 transactivation in this setting is due to an alternative signaling system rather than through a p53-dependent mechanism. p53 responds to different forms of cellular stress by targeting and activating genes involved in growth arrest and cell death. A target of p53-induce transcription is the p21/WAF1 gene, which encodes a cyclin-dependent kinase inhibitor (1). In addition, levels of p53 are tightly regulated by mdm2, which binds to p53 repressing its activity and triggering its degradation. The MDM2 gene is itself under the transcriptional control of p53, creating an autoregulatory feedback loop (2).

Alterations in the TP53 gene appear to be uncommon in prostate cancer, and their clinical significance has not been fully investigated. A recognized limitation of most studies is that they are confined to the analysis of p53 alterations, without analyzing other critical components that regulate its functions. The MDM2 gene is amplified in a variety of tumors, and mdm2 overexpression without amplification appears to be a common mechanism of p53 inactivation in certain cancers (3,4). Lack of data regarding the functional status of the p53 products encountered in the tumors analyzed represents another drawback. It has been reported that p21/WAF1 gene expression may serve as an indicator of p53 activity, since p21/WAF1 is under the transcriptional control of p53. However, serum or individual growth factors, such as epidermal growth factor (EGF), and fibroblast growth factor (FGF), were shown to induce p21 expression in p53-deficient cells (5,6). Thus, there are at least two separate pathways accounting for the induction of p21, one linked to DNA-damage recognition, and the other produced by signaling mechanisms caused by certain cellular mitogens.

In the present study, we have analyzed the patterns of p53 expression and those of critical components of its pathway, namely mdm2 and p21, in 86 patients with prostate cancer. The association between these markers and clinicopathological parameters of poor outcome, including time to PSA relapse and proliferative index, were also examined.

Experimental Details

Experimental Details for Second Series of Experiments

Materials and Methods

Patients. A total number of 86 patients who underwent radical prostatectomy at Memorial Sloan-Kettering Cancer Center in the period between 1990 through 1991 were studied. Patient selection was based on the availability of both adequate clinical follow up and representative archival pathological materials for immunohistochemical analysis. The median age at the time of surgery was 65 years (range 46–74). Their median follow up was 64.5 months (range 10–94 months). Formalin-fixed, paraffin embedded prostate tissues were obtained from our archival tumor bank. Representative hematoxylin-eosin stained sections were examined to evaluate the histopathological characteristics of each case.

Clinicopathological parameters examined include pretreatment PSA, pathologic stage and Gleason score, both determined based on the radical prostatectomy specimen. Time to PSA relapse was calculated from the day of surgery to the first detectable PSA. PSA relapse was defined as three consecutive rise in PSA at least one week apart. Only patients who had undetectable PSA level after surgery were included in this analysis.

Tumors were staged pT2 (n=51) and pT3 (n=35). Twenty-nine patients were Gleason score <7, while 18 patients were Gleason ≧7. In six cases, due to scarcity of tumor representation in the specimen, grade was considered to be not interpretable. Thirty-three patients (3E.3%) received neoadjuvant hormone treatment preoperatively, and were defined as hormone-treated. These patients had non-evaluable Gleason scores. Patients who did not receive neoadjuvant hormone treatment were defined as hormone-naive.

Monoclonal Antibodies and Immunohistochemistry. The following well characterized mouse monoclonal antibodies and corresponding final working dilutions were used for the present study: anti-p53 monoclonal antibody PAB1801 (Ab-2 clone; CalBiochem/Oncogene Science, Boston, Mass.; 1:500 dilution); anti-mdm2 monoclonal antibody 2A10 (a gift from Dr. Arnold Levine, Rockefeller University, New York, N.Y.; 1:500 dilution); and an anti-p21 monoclonal antibody (Ab-1 clone; CalBiochem/Oncogene Science; 1:20 dilution). An anti-Ki67 mouse monoclonal antibody (clone MIB1; Immunotech SA, France; 1:50 dilution) was used to assess proliferative index. MIgS-Kp1, a mouse monoclonal antibody of the same subclass as the primary antibodies listed above was used as negative control.

An avidin-biotin immunoperoxidase method was utilized. Briefly, sections were subsequently immersed in boiling 0.01% citric acid (pH 6.0) for 15 minutes to enhance antigen retrieval and incubated with primary antibodies overnight at 4° C. Biotinylated horse anti-mouse IgG antibodies were applied for 1 h (Vector Laboratories, Burlingame, Calif.; 1:500 dilution), followed by avidin-biotin peroxidase complexes for 30 minutes (Vector Laboratories; 1:25 dilution). Diaminobenzidine was used as the final chromogen and hematoxylin was used as the nuclear counterstain. Nuclear immunoreactivity were classified on a continuous scale with values that ranged from undetectable levels or 0% to homogeneous staining or 100%.

Statistical Analysis. The three markers were analyzed both as percentage of tumor cells and as discrete variables based on a priori cut-points. The cut-point for p53 of >20% was based on our previous analysis of p53 alterations in bladder cancer that revealed a strong association between p53 point mutation and p53 nuclear accumulation in >20% of tumor cells (7,8). For mdm2, the cut-point was based on what have been published correlating mdm2 overexpression in ≧20% of tumor cells with worse clinicopathological parameters (9,10) The same principle applied to the Ki67 cut-point determination (11,12). For p21 the cut-point of >5% was based on our finding that normal prostate glands lack p21 expression, and the observation of p21 nuclear staining and presence of mitotic figures indicating high proliferative activity of the tumors.

The association of percentage of tumor cells expressing the markers with time to PSA relapse, while adjusting for other variables with known prognostic significance, was assessed using the Cox proportional hazards model (13). In addition, Kaplan-Meier estimation (14) was performed and the log rank test (15) employed to assess the univariate relationship between the individual markers using cut points and time to PSA relapse.

The associations between Gleason group and the three biomarkers were assessed using Fisher's exact test (16). Also, associations between the three markers and variables such as Ki67 proliferative index, stage, and hormone status were also assessed using the above test.

Experimental Results

Experimental Results for the Second Series of Experiments

Table 1 summarizes the data in relation to clinicopathological parameters, including pre-treatment PSA, tumor stage, Gleason tumor grade, hormone status, proliferative index, and immunophenotype profile. FIG. 7 illustrates the univariate relationships of the three markers with time to PSA relapse with Kaplar-Meier curves estimated.

TABLE 1

Summary Of Data In Relation To Immunophenotype Profile

| | P53 | | p21 | | mdm-2 | |
|---|---|---|---|---|---|---|
| | (#) | (%) | (#) | (%) | (#) | (%) |
| PSA | | | | | | |
| <4 | 0/18 | 0 | 5/18 | 27 | 3/18 | 16 |
| 4–10 | 3/28 | 10 | 7/28 | 25 | 7/28 | 25 |
| >10 | 3/40 | 7.5 | 16/40 | 40 | 18/40 | 45 |
| p value | | .374 | | .382 | | .060 |
| Stage | | | | | | |
| T < 3 | 3/51 | 5.8 | 14/51 | 27 | 11/51 | 21 |
| T = 3 | 3/35 | 8.5 | 14/35 | 40 | 17/35 | 48 |
| p value | | .631 | | .222 | | .009 |
| Gleason Score | | | | | | |
| <7 | 0/29 | 0 | 7/29 | 24 | 7/29 | 24 |
| =7 | 2/18 | 11 | 10/18 | 22 | 9/18 | 50 |
| NE | 4/33 | 2 | 10/33 | 30 | 11/33 | 33 |
| p value | | .157 | | .074 | | .190 |

TABLE 1-continued

Summary Of Data In Relation To Immunophenotype Profile

| | P53 | | p21 | | mdm-2 | |
|---|---|---|---|---|---|---|
| | (#) | (%) | (#) | (%) | (#) | (%) |
| Hormone Status | | | | | | |
| Naive | 2/53 | 3 | 18/53 | 33 | 17/53 | 32 |
| Treated | 4/33 | 12 | 10/33 | 30 | 11/33 | 33 |
| p value | | .139 | | .725 | | .904 |
| Proliferation Index Ki67 | | | | | | |
| Low | 5/75 | 6 | 20/75 | 26 | 22/75 | 29 |
| High | 1/11 | 9 | 8/11 | 72 | 6/11 | 54 |
| p value | | .768 | | .002 | | .096 | p53 nuclear overexpression of >20% was observed in 6 of 86 cases. The distribution of p53% expression was primarily patients expressing less than 5% p53 (n=76). The other 10 patients had varying levels of p53% expression, indicating a very low frequency of p53 alteration in this group of patients. There is no correlation between p53 positive phenotype and pretreatment PSA, tumor stage, tumor grade, hormone status, or high proliferative index. Also, there is no association between p53 overexpression and p21 or mdm2 overexpression. A significant association was observed between p53 status determined by the cut-point and time to PSA relapse. This association is illustrated in FIG. 7. Using the log rank test to examine the overall differences between p53 negative phenotype and p53 positive phenotype revealed a statistical significant difference P<0.01. This indicates an obvious PSA relapse time advantage for patients who do not overexpress p53. However, the magnitude of this difference may not be reliably estimated due to the small number of patients and events in the p53 positive phenotype group.

mdm2 nuclear overexpression of ≧20% tumor cells was observed in 28 of 86 cases (32.5%). mdm2 positive phenotype was associated with advanced stage (P=0.009). In addition, mdm2 overexpression was observed not to be significant with respect to a decreased time to PSA relapse (FIG. 7). A trend was observed between mdm2 overexpression and higher pretreatment PSA (P=0.06).

p21 nuclear overexpression of >5% tumor cells was observed in 28 of 86 patients (32.5%). Patients with p21 positive phenotype were observed to have a significant association with high Ki67 proliferative index (P=0.002). High Ki67 proliferative index was identified in 11 of 86 patients (12.7%). Patients with p21 positive phenotype had a significant association with decreased time to PSA relapse, as illustrated in FIG. 7. Also, p21 overexpression was associated with mdm2 overexpression (P<0.01). However, no association was observed between identification of p21 and/or mdm2 positive phenotype and p53 overexpression.

Forty-three of the total 86 patients had one or more altered markers. Patients with any alteration (p53 or mdm2 or p21) were observed to have a higher rate of PSA relapse (P<0.01).

The multivariate relationship between the markers and time to PSA relapse was assessed using Cox proportional hazards model. It was of interest to examine the effect of the markers while adjusting for variables with know prognostic significance. Both, p53 and p21 positive phenotypes were significant while adjusting for pre-treatment PSA and Gleason group (P<0.01 for both markers). Examination of the overexpression of at least one marker (p53, mdm2 or p21) with respect to time to PSA relapse showed that this variable was also significant (P<0.01) while adjusted for pretreatment PSA and Gleason group. Tumor stage (<3 vs. ≧3) was not significant in either the univariate or multivariate analyses, and was thus excluded from the model. The model that seemed to account for the most information included p53 and p21, along with pre-treatment PSA.

Experimental Discussion

Experimental Discussion for the Second Series of Experiments

Reports dealing with the frequency of TP53 mutations and p53 overexpression in prostate cancer have yielded conflicting results, alterations ranging from 2% to 65% of cases studied (17–21). This discrepancy might be explained by the relatively small number of cases and different disease stages analyzed in some reports, the distinct methodologies employed, and the cutoff points used for evaluation of IHC results. However, a general finding was the association between p53 alterations and clinicopathological parameters of poor clinical outcome, such as high grade and late stage (18,19,22). In this study, we observed a relatively low frequency of p53 nuclear overexpression in patients with localized prostate cancer, as previously reported (23,24). To determine the potential clinical relevance of identifying a p53 positive phenotype, we correlated phenotypic characteristics of the tumors with the time to PSA relapse. This is considered the most sensitive indicator of success or failure following radical prostatectomy in patients treated for localized disease. Analysis of data revealed that p53 overexpression was significantly associated with PSA relapse (P<0.01) and independent of pretreatment PSA and Gleason group. However, the magnitude of this difference may not be reliably estimated due to the small number of patients and events in the positive phenotype. We also observed that all patients who received neoadjuvant hormone treatment prior to surgery and had tumors that overexpressed p53 relapsed. This finding could be due to the advanced stage at which patients presented and were selected for treatment using this modality. Mechanistically, an altered p53 status in this setting could have conferred resistance to castration-induced apoptosis, ultimately leading to disease relapse. The association between p53 overexpression and hormone refractory prostate cancer has been reported in locally advanced and metastatic disease (25). However, to our knowledge, this is the first report to suggest that this association might be an early event in the evolution of hormone refractory disease in clinically localized prostate cancer.

In the present study we also analyzed alterations affecting other regulators of the p53 pathway in primary prostate cancer, including mdm2 and p21. The MDM2 gene maps to 12q13 and is found overexpressed in certain tumors, due to its amplification as a component of an amplicon that includes other relevant genes, such as CDK4. The MDM2 is under transcriptional regulation by p53, and encodes a 90-kDa zinc finger protein (mdm2) which contains a p53-binding site (26). It has been shown that mdm2 binds to p53, and acts as a negative regulator by inhibiting p53 transcriptional activity and targeting its degradation, thus creating an autoregulatory feedback loop (27). In this study, nuclear mdm2 overexpression was found in 32.5% of cases. We observed that mdm2 positive phenotype was significantly associated with advanced stage. It has been previously reported that MDM2 is not amplified on primary prostate cancer, based on a study of 29 tumors analyzed by Southern blot hybridization (28). The discrepancy between the rate of MDM2 gene amplification and protein overexpression has been described in Burkitt's lymphoma and breast cancer (29,30). Furthermore, it was observed in soft tissue sarcomas that mdm2 overexpression rather than its amplification, was associated with worse clinical outcome (10). Based on data from this study, we can postulate that mdm2 overexpression is a frequent mechanism of p53 inactivation in prostate cancer, and in this context the MDM2 gene can be classified as an oncogene in this setting.

The p21/WAF1 gene encodes a nuclear protein member of the cyclin-dependent kinase inhibitory KIP family involved in senescence and cell quiescence (31). The p21/WAF1 gene is also transcriptionally regulated by p53. However, p21 induction could also be accomplished by a p53-independent pathway. Serum or individual growth factors, such as EGF and FGF, were shown to induce p21 in p53-deficient cells (32). Based on these data, it has been postulated that p21 induction could be activated through two separate pathways. The rate of p21/WAF1 mutations in human cancer is very low (33). However, there is an association between altered patterns of p21 expression and clinical outcome in certain tumors, such as bladder, colon, and heptocellular carcinomas (34–36). Lack of p21 expression in these studies was correlated with poor clinical outcome, an expected finding if one postulates that p21 deficiency reflects p53 inactivation. As a corollary to this hypothesis, the p21 negative phenotype observed in the above referred studies was usually associated with p53 alterations. However, in our study we found that p21 positive phenotype was significantly associated with high proliferative index and mdm2 overexpression, but not with p53 status. Moreover, patients with p21 positive phenotype had a significant association with decreased time to PSA relapse. p21 overexpression has been reported to be associated with worse prognosis in other tumor types, including, breast, esophageal carcinoma, and squamous cell carcinomas of head and neck (37–39). Moreover, p21 overexpression was found to be associated with resistance to chemotherapy in acute myeloid leukemia and glioblastoma (40,41).

These data could be interpreted as follows (see FIG. 8). A positive p21 phenotype could signify activation of p53 in response to DNA damage or cellular stress. This effect would result in G1 arrest of the prostate tumor cells expressing p21. We observed, on the contrary, an association between p21 positive phenotype and increased proliferative activity. Thus, it is more plausible to postulate that the p21 overexpression observed is caused by a p53-independent transactivation mechanism. In the setting of prostate cancer, the alternative mechanism could be due to mitogenic stimuli via growth factor signaling. There is abundant evidence regarding the upregulation of growth factor receptor/ligand activity in prostate tumors (42–46). An additional aberration causing p53 inactivation would be required in this model to explain the lack of cell death and association with proliferative activity. It is our hypothesis that the increased mdm2 expression discussed above provides this requirement, further supporting the oncogenic role of mdm2 in prostate cancer.

Finally, the association between p21 and high proliferative index might also reflect deregulated cyclinD1/CDK4 activity. In fact, we observed a strong association between p21 positive phenotype and cyclin D1 overexpression in this cohort of patients (Drobnjak et al., personal communication). Taken together, these data supports the concept that p21 overexpression denotes an inefficient pRB control on S-phase entry.

Growth control in mammalian cells is accomplished largely by the action of the RB protein, regulating exit from the G1 phase, and the p53 protein, triggering growth arrest or apoptotic processes. In this group of patients, there is enough evidence to suggest that both mechanisms are defective in prostate cancer. The high proliferative index reflects the inefficient pRB control. We postulate that this phenomenon is produced by deregulated cyclinD1/CDK4 activity, which is associated with a p21 positive phenotype. The deactivation of a p53-dependent apoptosis could be explained by the degradation of p53 induced by mdm2 overexpression.

In sum, alterations affecting the p53 pathway are frequent events in prostate cancer. It is our hypothesis that a pathway of prostate cancer progression involves p53 inactivation caused by mdm2 overexpression, and that p21 transactivation in this setting is due to an alternative signaling system rather than through a p53-dependent mechanism.

References for Second Series of Experiments

1. Cordon-Cardo, C. Mutation of cell cycle regulators. Biological and clinical implication for human neoplasms. Am J Pathol, 147: 545–560,1995.
2. Momand, J., Zambetti, G. P., Olsen, D. C., George, D. L., and Levine A. J. The MDM2 oncogene products forms a complex with the p53 protein and inhibits p53-mediated transactivation. Cell, 69:1237–1245,1992.
3. Lianes, P., Orlow, I., Zhang, Z-F., Oliva, M., Sarkis, A., Reuter, V., and Cordon-Cardo., C. Altered patterns of MDM2 and TP53 expression in human bladder cancer. J Natl. Cancer Inst., 86:1325–1330, 1994.
4. Gorgoulis, V. G., Rassidakis, G. Z., Karameris, A. M., Papastamatiou, H., Trigidou, R., Veslemes, M., Rassidakis, A. N., and Kittas, C. Immunohistochemical and molecular evaluation of the mdm2 gene product in bronchogenic carcinoma. Mod Pathol,9:544–554,1996.
5. Sinicrope, F. A., Roddey, G., Lemoine, M., Ruan, S., Stephens, L. C., Frazier, M. L., Shen, Y., and Zhang,W. Loss of p21WAF1/Cip1 protein expression accompanies progression of sporadic colorectal neoplasms but not hereditary nonpolyposis colorectal cancers. Clin Cancer Res, 4:1251–1261,1998.
6. Lacombe, L., Orlow, I., Zhang, Z-F, Oliva, M., Sarkis, A., Reuter, V. G, and Cordon-Cardo, C. Analysis of p21WAF1/CIP1 in primary bladder tumors. Ocol Res, 8:409–414,1996.
7. Sarkis, A. S., Dalbagni, G., Cordon-Cardo, C., Zhang, Z-F., Sheinfeld, J., Fair, W. R., Herr, H. W., and Reuter, V. E. Nuclear overexpression of p53 protein in transitional cell bladder carcinoma: a marker for disease progression. J Natl. Cancer Inst., 85:53–59, 1993.
8. Cordon-Cardo, C., Dalbagni, G., Saez, G. T., Oliva, M. R., Zhang, Z-F., Rosai, J., Reuter, V. E., and Pellicer, A. p53 mutations in human bladder cancer: genotypic versus phenotypic patterns. Int J. Cancer, 56:347–353, 1992.
9. Osman, I., Scher, H. I., Zhang, Z-F., Pellicer, I., Hamza, R., Eissa, S., Khaled, H., and Cordon-Cardo, C. Alterations affecting the p53 control pathway in Bilharzial-related bladder cancer. Clin Cancer Res, 3:531–536,1997
10. Cordon-Cardo, C., Latres, E., Drobnjak, M., Oliva, M. R., Pollack, D., Woodruff, J. M, Marechal, V., Chen, J., Brennan, M. F., and Levine, A. J. Molecular abnormalities of mdm2 and p53 genes in adult soft tissue sarcomas. Cancer Res, 54:794–799, 1994.
11. Heslin, M. J., Cordon-Cardo, C., Lewis, J. J., Woodruff, J. M., and Brennan, M. F. Ki67 detected by MIB-1 predicts distant metastasis and tumor mortality in primary, high grade extremity soft tissue sarcoma. Cancer, 83:490–497, 1998.
12. Osman, I., Scher, H., Zhang, Z-F., Soos, T. J., Hamza, R., Eissa, S., Khaled, H., Koff, A., and Cordon-Cardo, C. Expression of cyclin D1, but not cyclins E and A, is related to progression in Bilharzial bladder cancer. Clin Cancer Res, 3:2247–2251, 1997.
13. Cox, D. R. Regression models and life tables. J Royal Statistical Scoc, 34:187–220,1972.
14. Kaplan, E. L. and Meier, P. Nonparametric estimation from incomplete observations. J American Statistical Assoc, 53:457–481,1958.
15. Mantel, N. Evaluation of survival data and two new rank order statistics arising in its consideration. Cancer Chemo Reports,50:163–170,1966.
16. Agresti, A. Categorical data Analysis.pp39–44. Wiley, New York 1996.
17. Hall, M. C, Navone, N. M., Troncoso, P., Pollack, A., Zagars, G. K., von Eschenbach, A. C., Conti, C. J., and Chung, L. W. Frequency and characterization of p53 mutations in clinically localized prostate cancer. Urology, 45:470–475,1995.
18. Kubota, Y., Shuin, T., Uemura, H., Fujinami, K., Miyamoto, H., Torigoe, S., Dobashi, Y., Kitamura, H., Iwasaki, Y., and Danenberg, K. Tumor suppressor gene p53 mutations in human prostate cancer. Prostate, 27:18–24, 1995.
19. Hughes, J. H., Cohen, M. B., and Robinson, R. A. p53 immunoreactivity in primary and metastatic prostatic adenocarcinoma. Mod Pathol, 8:462–466, 1995.
20. Theodorescu, D., Broder, S. R., Boyd, J. C., Mills, S. E., and Frierson, H. F Jr. p53, bcl-2 and retinoblastoma proteins as long-term prognostic markers in localized carcinoma of the prostate. J Urol, 158:131–137,1997.
21. Gumerlock, P. H., Chi, S. G., Shi, X. B., Voeller, H. J., Jacobson, J. W., Gelmann, E. P., and devere White, R. W. p53 abnormalities in primary prostate cancer: single-strand conformation polymorphism analysis of complementary DNA in comparison with genomic DNA. The Cooperative Prostate Network. J Natl Cancer Inst., 89:66–71, 1997
22. Bauer, J. J., Sesterhenn, I. A., Mostofi, F. K., McLeod, D. G., Srivastava, S., and Moul, J. W. Elevated levels of apoptosis regulator proteins p53 and bcl-2 are independent prognostic biomarker in surgically treated clinically localized prostate cancer. J Urol , 156:1511–1516, 1996.
23. Sinik, Z., Alkibay, T., Ataoglu, O., Biri, H., Sozen, S., Deniz, N., Karaoglan, U., and Bozkirli, I. Nuclear p53 overexpression in bladder, prostate, and renal carcinomas. Int J Urol,4:546–551,1997
24. Brooks, J. D., Bova, G. S., Ewing, C. M., Piantadosi, S., Carter, B. S., Robinson, J. C., Epstein, J I, and Isaacs, W. B. An uncertain role for p53 gene alterations in human prostate cancers. Cancer Res, 56:3814–3822, 1996.
25. Srivastava, S., and Moul, J. W. p53 tumor suppressor gene alteration in prostate cancer and potential gene therapy approaches. Molecular Urolog, 1:151–158, 1997.
26. Kubbutat, M. H. G., Ludwig, R. L., Ashcroft, M., Vousden, K. H. Regulation of Mdm2-directed degradation by the C terminus of p53. Mol Cell Biol, 18:5690–5698, 1998.
27. Grossman, S. R., Perez, M., Kung, A. L., Joseph, M., Mansur, C., Xiao, Z. X., Kumar, S., Howley, P. M., and Livingston, D. M. p300/MDM2 complexes participate in MDM2-mediated p53 degradation. Mol Cell, 2:405–415, 1998.
28. Ittmann, M., Wieczorek, R., Heller, P., Dave, A., Provet, J., and Krolewski, J. Alterations in the p53 and MDM-2 genes are infrequent in clinically localized, stage B prostate adenocarcinomas. Am J Pathol, 145:287–293, 1994.
29. Capoulade, C., Bressac-de Paillerets, B., Lefrere, I., Ronsin, M., Feunteun , J., Tursz, T., Wiels, Overexpres- 29. sion of MDM2, due to enhanced translation, results in inactivation of wild-type p53 in Burkitt's lymphoma cells. Oncogene, 16:1603–1610,1998.
30. Bueso-Ramos, C. E., Manshouri, T., Haidar, M. A., Yang, Y., McCown, P., Ordonez, N., Glassman, A., Sneige, N., and Albitar, M. Abnormal expression of MDM-2 in breast carcinomas. Breast Cancer Res Treat, 37:179–188, 1996.
31. Kuzumaki, T., Kobayashi, T., and Ishikawa, K. Genistein induces p21(Cip1/WAF1) expression and blocks the G1 to S phase transition in mouse fibroblast and melanoma cells. Biochem Biophys Res Commun 251:291–295, 1998.
32. Fan, Z., Shang, B. Y., Lu, Y., Chou, J. L., and Mendelsohn, J. Reciprocal changes in p27(Kip1) and p21(Cip1) in growth inhibition mediated by blockade or overstimulation of epidermal growth Factor receptors. Clin Cancer Res, 3:1943–1948,1997.
33. Elbendary, A. A., Cirisano, F. D., Evans, A. C Jr., Davis, P. L., Iglehart, J. D., Marks, J. R., and Berchuck, A. Relationship between p21 expression and mutation of the p53 tumor suppressor gene in normal and malignant ovarian epithelial cells. Clin Cancer Res, 2:1571–1575, 1996.
34. Stein, J. P., Ginsberg, D. A., Grossfeld, G. D., Chatterjee, S. J., Esrig, D., Dickinson, M. G., Groshen, S., Taylor, C. R., Jones, P. A., Skinner D. G., and Cote, R. J. Effect of p21WAF1/CIP1 expression on tumor progression in bladder cancer. J Natl. Cancer Inst., 90:1072–1079, 1998.
35. Valassiadou, K. E., Stefanaki, K., Tzardi ,M., Datseris, G., Georgoulias, V., Melissas, J., Tsiftsis, D. D., Delides, G., Kanavaros, P. Immunohistochemical expression of p53, bcl-2, mdm2 and waf1/p21 proteins in colorectal adenocarcinomas. Anticancer Res, 17:2571–2576,1997.
36. Qin, L. F., Ng, I. O., Fan, S. T., and Ng, M. p21/WAF1, p53 and PCNA expression and p53 mutation status in hepatocellular carcinoma. Int J Cancer 79:424–428, 1998.
37. Caffo, O., Doglioni, C., Veronese, S., Bonzanini, M., Marchetti, A., Buttitta, F., Fina, P., Leek, R., Morelli, L., Palma, P. D., Harris, A. L., and Barbareschi, M. Prognostic Value of p21(WAF1) and p53 Expression in Breast Carcinoma: An Immunohistochemical Study in 261 Patients with long-term Follow-Up. Clin Cancer Res, 2:1591–1599,1996.
38. Sarbia, M., Stahl, M., Hausen, A. Z., Zimmermann, K., Wang, L., Fink, U., Heep, H., Dutkowski, P., Willers, R., Muller, W., Seeber, S., and Gabbert, H. Expression of p21 predicts outcome of esophageal cancer patients treated by surgery alone or by combination therapy modalities. Clin Cancer Res, 4:2615–2623,1998.
39. Erber, R., Klein, W., Andl, T., Enders, C., Born, A. I., Conradt, C., Bartek, J., and Bosch, F. X. Aberrant p21 (CIP1/WAF1) protein accumulation in head-and-neck cancer. Int J Cancer, 74:383–389,1997.
40. Zhang, W., Kornblau, S. M., Kobayashi, T., Gambel, A., Claxton, D., and Deisseroth, A. B. High levels of constitutive WAF1/Cip1 protein are associated with chemoresistance in acute myelogenous leukemia. Clin Cancer Res, 1:1051–1057,1995.
41. Ruan, S., Okcu, M. F., Ren, J. P., Chiao, P., Andreeff, M., Levin, V., and Zhang, W. Overexpressed WAF1/Cip1 renders glioblastoma cells resistant to chemotherapy agents 1,3-bis(2-chloroethyl)-1-nitrosourea and cisplatin. Cancer Res, 58:1538–1543,1998.
42. Tanaka, A., Furuya, A., Yamasaki, M., Hanai, N., Kuriki, K., Kamiakito, T., Kobayashi, Y., Yoshida, H., Koike, M., and Fukayama M. High frequency of fibroblast growth factor (FGF) 8 expression in clinical prostate cancers and breast tissues, immunohistochemically demonstrated by a newly established neutralizing monoclonal antibody against FGF 8. Cancer Res, 58:2053–2056,1998.
43. Peehl, D. M., and Sellers, R. G. Basic FGF, EGF, and PDGF modify TGFbeta-induction of smooth muscle cell phenotype in human prostatic stromal cells. Prostate, 35:125–134,1998.
44. Culig, Z., Hobisch, A., Cronauer, M. V., Radmayr, C., Hittmair, A., Zhang, J., Thurnher, M., Bartsch, G., and Klocker, H. Regulation of prostatic growth and function by peptide growth factors. Prostate, 28:392–405,1996.
45. Scher, H. I., Sarkis, A., Reuter, V., Cohen, D., Netto, G., Petrylak, D., Lianes, P., Fuks, Z., Mendelson, J., and Cordon-Cardo, C. Changing pattern of expression of the epidermal growth factor receptor and transforming growth factor alpha in the progression of prostatic neoplasms. Clin Cancer Res 1:545–550,1995.
46. Cohen, D. W., Simak, R., Fair, W. R., Melamed, J., Scher, H. I., and Cordon-Cardo, C. Expression of transforming growth factor-alpha and the epidermal growth factor receptor in human prostate tissues. J Urol 152:2120–2124,1994.

Third Series of Experiments

Cyclin D1 is a key regulator of the G1 phase progression of the cell division cycle. There is an increasing evidence that deregulated cyclin D1 expression is implicated in tumorigenesis and tumor progression in certain neoplasms. The present study was conducted in order to analyze the alterations affecting cyclin D1 in prostate cancer, as well as to assess its potential clinical significance. We studied 116 cases of primary (n=86) and metastatic (n=30) prostate carcinomas using immunohistochemistry and a well characterized monoclonal antibody to cyclin D1. The results were correlated with proliferative index, as assessed by Ki67 antigen expression and with clinicopathologic variables of poor prognosis. Cyclin D1 positive phenotype, defined as identification of immunoreactivity in the nuclei of $\geq 20\%$ tumor cells, was found in 26 of 116 (22%) cases. A significant association was observed between cyclin D1 positive phenotype and clinicopathologic parameters, such as advanced tumor stage (T$\geq$3) (P=0.045), evidence of bone metastases (P=0.001) and with elevated preoperative prostate specific antigen measurements (PSA>10 ng/ml) (P=0.01). Ki67 proliferative index was considered high when $\geq 20\%$ tumor cells displayed positive nuclear staining, a phenotype that was observed in 20 of 107 (19%) evaluable cases. Moreover, high Ki67 proliferative index was associated with cyclin D1 overexpression (P=0.01). These data support the hypothesis that alterations of cyclin D1 may represent an oncogenic event in human prostate cancer. Furthermore, it appears that cyclin D1 overexpression contributes to tumor progression in a subset of particularly aggressive prostate carcinomas, especially those developing osseous metastases.

Prostate cancer has been reported to be a neoplastic disease of a slow growth rate. Nevertheless, it still represents the second leading cause of cancer deaths in men in the United States. There is an obvious discrepancy between the clinical impression of a slowly growing neoplasm and tendency to produce an aggressive metastatic disease in individual patients. The prognostic indicators of histologic grade, pathologic stage, DNA ploidy, and tumor cell proliferative index proved to be of limited value in determining the biologic behavior of prostate cancer (1–3). Tumor suppressor genes, particularly p53 and RB, implicated in the molecular genetics of many human malignancies, were reported to be altered in a rather low frequency in prostate cancer (4–8).

Cell cycle transitions are controlled by functional heterodimers composed of a cyclin, acting as a regulatory subunit, and cyclin-dependent kinase (Cdk), which acts as the catalytic component (9). Multiple cyclins have been isolated and characterized, and a temporal map of their expression has been delineated. It is postulated that the complexes formed by cyclin D1 and Cdk4 govern G1 progression, while cyclin E-Cdk2 controls entry into S-phase and cyclin A-Cdk2 affects the regulation through S-phase (10). Cyclin D1-Cdk4 complexes exert their function through the phosphorylation of the product encoded by the retinoblastoma gene, pRb, in order to overcome the cell cycle block imposed by hypophosphorylated pRb (10). Several studies suggest that gene amplification and overexpression of cyclin D1 and Cdk4 are oncogenic events in certain tumors, including breast cancer (11), head and neck tumors (12, 13), esophageal (14, 15) and colorectal carcinoma (16). We undertook this study in order to analyze patterns of cyclin D1 expression in prostate cancer. The alterations identified were correlated with Ki67 proliferative index, as well as relevant clinicopathologic parameters, in an attempt to define their potential biologic significance in prostate cancer.

Experimental Details
Experimental Details for Third Series of Experiments
Material and Methods Patients Characteristics and Tissues. A cohort of 116 patients with prostate carcinoma were evaluated, consisting of 86 primary and 30 metastatic cases (eight metastases to lymph node and 22 metastases to bone). All primary tumors (n=86) represented consecutive cases of patients who underwent radical prostatectomy at Memorial Sloan-Kettering Cancer Center, in the period of 1990 and 1991. All metastatic cases (n=30) were selected on the basis of the availability of tissue in the tumor bank. Samples were formalin-fixed, paraffin embedded tissue specimens, obtained from the Department of Pathology at Memorial Sloan-Kettering Cancer Center. Representative hematoxylineosin stained sections of each paraffin block were examined microscopically to confirm the presence of tumor, as well as to evaluate the pathologic grade and stage of the tumors analyzed. Thirty-three of 86 patients with primary carcinoma received preoperatively neoadjuvant hormone therapy (hormone treated), while the remaining 53 patients were not treated with such protocols and were considered hormone-naive. Hormone-naive primary tumors with sufficient tumor representation on tissue sections were assigned histologic grade (n=47). Histologic grade was categorized into two groups: low grade (Gleason score <7), and high grade (Gleason score ≧7). According to pathologic stage, cases were grouped into early (organ confined tumors, $T_2$), or advanced tumors (extending beyond prostatic capsule, $\geq T_3$). The response variable time to prestate-specific antigen (PSA) relapse was defined as the time from radical prostatectomy to the time of the first detectable (non zero) PSA measurement. Three consecutive increases of PSA were required to confirm PSA relapse. Only patients who had a nonmeasurable PSA after radical prostatectomy were included in the analysis.

Monoclonal Antibodies and Immunohistochemistry. The following well characterized antibodies and corresponding final working concentrations were used for the present study: anti-cyclin D1 mouse monoclonal antibody (Ab-3, clone DCS-6, IgG1, Oncogene, Calbiochem, Cambridge, Mass.; 1 µg/ml); anti-Ki67 mouse monoclonal antibody (clone MIB-1, IgG1, Immunotech, Marseille, France; 4 µg/ml). A nonspecific mouse IgG1 kappa monoclonal antibody was used as a negative control at similar working concentrations. Immunohistochemistry was performed on 5 µm tissue sections using avidin-biotin-peroxidase method and antigen retrieval. Briefly, sections were immersed in boiling 0.01 M citric acid (pH 6.0) and heated in microwave oven for 15 minutes, to enhance epitope exposure. After cooling to room temperature, slides were incubated with 10% normal horse serum for 30 minutes. Subsequently, appropriately diluted primary antibodies were applied for overnight incubation at 4° C. Biotinylated horse anti-mouse IgG antibodies were used as secondary reagents, applied for an incubation period of 30 minutes (Vector Laboratories, Burlingame, Calif.; 1:500 dilution), followed by avidin-biotin-peroxidase complexes incubated for 30 minutes (Vector Laboratories—1:25 dilution). Diaminobenzidine was used as the final chromogen and hematoxylin as the nuclear counterstain.

Immunohistochemistry Evaluation. Nuclear immunoreactivities for both cyclin D1 and Ki67 antigens, were classified into two categories defined as follows: negative (<20% tumor cells displaying nuclear immunostaining), and positive (≧20% tumor cells with nuclear immunostaining). The appropriateness of this cutoff point was validated graphically by using predicted survival time and looking at specific immunoreactivities as a continuum data in this group of patients. Ultimately, results were interpreted as defined above.

Statistical Methods. The baseline variables examined were PSA (ng/ml) at time of diagnosis (divided into three categories: <4, 4–10 and >10), Tumor grade (Gleason score) (divided into two mutually exclusive categories: <7 or ≧7), Pathologic stage T (2 or ≧3), and percent cyclin D1 and Ki67 expression. Statistical analyses were conducted to assess: 1) the correlation between immunophenotypic variables and clinicopathologic parameters such as: presentation status, tumor grade, pathologic stage, preoperative PSA, and hormonal status; 2) the correlation among immunophenotypic variables; 3) association between immunophenotypes and PSA relapse free survival. The Mantel-Haenszel chi-square test was used to assess the associations among the different variables and results were considered significant if the P value was <0.05. The FREQ procedure in SAS was used for this study (17). The associations between time to PSA relapse and the immunophenotypes were evaluated using the Log Rank test and Kaplan Meier estimates (18).

Experimental Results
Experimental Results for the Third Series of Experiments

Table 2 summarizes immunohistochemical data in relation to clinicopathologic parameters. FIG. 9 illustrates the immunohistochemical staining patterns of cyclin D1 in representative cases of primary tumors and bone metastases.

TABLE 2

Clinicopathologic Parameters in Relation to Cyclin D1 Immunoreactivity

| Parameter | cyclin D1 − (<20%) | | cyclin D1 + (≧20%) | | Total | P-value |
|---|---|---|---|---|---|---|
| | N | (%) | N | (&) | | |
| Total Patients Presentation | 90 | (77.6) | 26 | (22.4) | 116 | |
| Primary tms | 76 | (88.4) | 10 | (11.6) | 86 | |
| LN metastases | 7 | (87.5) | 1 | (12.5) | 8 | NS |
| Primary tms | 76 | (88.4) | 10 | (11.6) | 86 | |
| Bone metastases | 7 | (31.8) | 15 | (68.2) | 22 | 0.001 |
| Ki67 proliferative index | | | | | | |
| Low (<20%) | 71 | (81.6) | 16 | (18.4) | 87 | |

TABLE 2-continued

Clinicopathologic Parameters in Relation to Cyclin D1 Immunoreactivity

| Parameter | cyclin D1 − (<20%) | | cyclin D1 + (≧20%) | | Total | P-value |
|---|---|---|---|---|---|---|
| | N | (%) | N | (&) | | |
| High (≧20%) | 11 | (55.0) | 9 | (45.0) | 20 | 0.01 |
| Primary tumors | 76 | (88.4) | 10 | (11.6) | 86 | |
| Tm. Grade (Gleason)* | | | | | | |
| Low (<7) | 27 | (93.1) | 2 | (6.9) | 29 | |
| High (≧7) | 17 | (94.4) | 1 | (5.6) | 18 | NS |
| Path. Stage | | | | | | |
| Early (T$_2$) | 48 | (94.1) | 3 | (5.9) | 51 | |
| Advanced (≧T$_3$) | 28 | (80.0) | 7 | (20.0) | 35 | 0.045 |
| Hormonal status | | | | | | |
| H. naive | 49 | (92.5) | 4 | (7.5) | 53 | |
| H. treated | 27 | (81.8) | 6 | (18.2) | 33 | NS |
| Pretreatment PSA | | | | | | |
| <4 ng/ml | 17 | (94.4) | 1 | (5.6) | 18 | |
| 4–10 ng/ml | 28 | (100.0) | 0 | (0.0) | 28 | |
| >10 ng/ml | 31 | (77.5) | 9 | (22.5) | 40 | 0.01 |

*Patients who had received neoadjuvant hormonal therapy (n = 33) and tissue sections with inadequate tumor representation (n = 6) were not assigned Gleason grade and were excluded from this analysis.

Cyclin D1 was expressed in ≧20% tumor cells in 26 of 116 (22%) evaluable cases, corresponding to 10 of 86 (12%) primary lesions and 16 of 30 (53%) metastases. There was a statistically significant association between cyclin D1 overexpression and the presence of bone metastases. We observed that 15 of 22 (68%) bone metastases lesions overexpressed cyclin D1, while only 10 of 86 (12%) primary tumors presented with this positive phenotype (p=0.001). Cyclin D1 overexpression was also associated with advanced pathologic stage in primary tumors. We found that 7 of 35 (20%) tumors of advanced stage (extending beyond the prostatic capsule, ≧T3) displayed cyclin D1 nuclear overexpression, compared to only 3 of 51 (6%) organ confined tumors (T$_2$) (P=0.045). Cyclin D1 was also detected at increased percentage of tumor cells in patients with high initial pretreatment PSA values. Nine of 68 (13%) patients with PSA ≧10 ng/ml were cyclin D1 positive compared to only 1 of 18 (5%) patients with PSA <4 ng/ml (P=0.01). There was no association between cyclin D1 overexpression and tumor grade (Gleason score) or hormonal status (hormone naive vs. hormone treated). In order to assess disease progression we evaluated the time to PSA failure after radical prostatectomy. There was no association between cyclin D1 nuclear overexpression and early relapse as defined by increased PSA measurements after radical prostatectomy in these group of patients (p=0.2).

Cyclin D1 overexpression correlated well with high Ki67 proliferative index, which was scored as being high in 20 of 107 (19%) evaluable tumors. Nine of 20 (45%) tumors displaying high Ki67 proliferative index also possessed cyclin D1 nuclear overexpression, while only 16 of 87 (18%) cases with low Ki67 proliferative index overexpressed cyclin D1 (P=0.01). Nevertheless, Ki67 proliferative index alone was not associated with clinicopathologic parameters of poor outcome in this cohort of patients.

Experimental Discussion
Experimental Discussion for the Third Series of Experiments Autopsy records show that by the age of 80, approximately 60–70% of men around the world, have histologic evidence of prostatic carcinoma (19). Although this fact indicates generally slow growing nature of this malignancy, there are vast differences in the progression rate and development of clinically evident or metastatic disease in these patients during their lifetime. Prostate cancer progression tends to follow periprostatic and perivascular penetration, invasion along perineural spaces, pelvic lymph node metastases and particularly bone metastases (20). Almost one fourth of newly diagnosed cases presents with lymph node and/or osseous metastases and only one fourth of those survive five years (21). We were interested in analyzing the molecular events that might be responsible for the progression of prostate cancer from indolent to a life threatening, metastatic disease.

Some earlier reports on determining prostate tumor proliferation, measured by flow cytometric S-phase fraction showed a positive predictive value of this variable and prostate cancer progression (2). Tumors that demonstrate a higher proliferation rate are more likely to grow to and beyond prostatic capsule and to produce distant metastases. Recently, the cell division cycle regulatory mechanisms and their oncogenic role have become a major focus of cancer research. There is ever growing literature on cyclins and their associated kinases and their role in tumorigenesis (22). Particularly D-family cyclins were implicated in specific human tumors. Bartkova et al. (23) report on a large group of various human malignancies, including carcinoma of the breast, uterus, colon, melanomas and soft tissue sarcomas, high proportion of which exhibit immunoreactivity for cyclin D1. By far the most frequent chromosomal abnormality that affects cyclin D1 in majority of tumors is DNA amplification that results in increased expression of the RNA transcripts and protein levels (24). In some tumor types, however, immunohistochemistry proved to be the most accurate technique in determining deregulated expression of cyclin D1 (11, 23). In this study we used immunohistochemistry to determine cyclin D1 expression in patients with prostate carcinoma. To our knowledge this first expression study on cyclin D1 in both primary tumors and bone metastases specimens. Only recently Kallakury et al (25) evaluated the expression of p34$^{cdc2}$ and cyclin D1 in patients with radical prostatectomy. Results were correlated with conventional markers of poor prognosis. The authors showed no association between cyclin D1 immunoreactivity and clinicopathologic parameters, such as tumor grade, pathologic stage, lymph node metastases and with disease free survival. Our data in this study, on the other hand, suggest the involvement of cyclin D1 in the progression of human prostate cancer. There was a remarkably significant difference in the levels of cyclin D1 expression between bone metastases and primary tumors. There was an association between cyclin D1 immunoreactivity and tumors with advanced pathologic stage. Cyclin D1 further correlated well with high Ki67 proliferative index. Taken together, these results support the theory that increased levels of cyclin D1 expression contribute to cell cycle imbalance with extremely shortened G1 phase and possibly with reduced cell requirements for growth factors to proliferate (26, 27). Subclones of tumor cells with elevated cyclins expression may acquire uncontrolled growth advantage and contribute to tumor progression.

In this study we conclude that cyclin D1 may play an oncogenic role in prostate cancer. Our data indicate that cyclin D1 is involved in tumor progression, particularly in a development of bone metastases. However, in order to determine the timeframe and prognostic value of this marker in prostate cancer, from the early onset to the evolution of metastatic disease, we intend to evaluate cyclin D1 immunophenotypes in paired samples of primary tumors and metastatic sites from the same patients.

References for Third Series of Experiments

1. Gleason, D. F. Histologic grading of prostate cancer: a perspective. Hum. Pathol., 23:273–279, 1992.
2. Visakorpi, T., Kallionemi, O-P., Paronen, I. Y. I., Isola, J. J., Heikkinen, A. I., and Koivula, T. A. Flow cytometric analysis of DNA ploidy and S-phase fraction from prostatic carcinomas: implications for prognosis and response to endocrine therapy. Br. J. Cancer, 64: 578–582, 1991.
3. Bubendorf, L., Sauter, G., Moch, H., Schmid, H.-P., Gasser, T. C., Jordan, P., and Mihatsch, M. J., Ki67 labeling index: an independent predictor of progression in prostate cancer treated by radical prostatectomy. J. Pathol., 178:437–441, 1996.
4. Isaacs, W. B., Carter, B. S., and Ewing, C. M. Wild-type p53 suppresses growth of human prostate cancer cells containing mutant p53 alleles. Cancer Res., 51:4716–4720, 1991.
5. Bookstein, R., Rio, P., Madreperla, S. A., Hong, F., Allred, C., Grizzle, W. E., and Lee, W.-H. Promoter deletion and loss of retinoblastoma gene expression in human prostate carcinoma. Proc. Natl. Acad. Sci. USA, 87:7762–7766, 1990.
6. Visakorpi, T., Kallionemi, O.-P., Heikkinen, A., Koivula, T., and Isola, J. Small subgroup of aggressive, highly proliferative prostatic carcinomas defined by p53 accumulation. J. Natl. Cancer Inst., 84:883–887, 1992.
7. Bookstein, R., MacGrogan, D., Hilsenbeck S. G., Sharkey, F., and Allred, C. D. p53 is mutated in a subset of advanced-stage prostate cancers. Cancer Res., 53:3369–3373, 1993.
8. Navone, N. M., Troncoso, P., Pisters, L. L., Goodrow, T. L., Palmer, J. L., Nichols, W. W., von Eschenbach, A. C., and Conti, C. J. p53 protein accumulation and gene mutation in the progression of human prostate carcinoma. J. Natl. Cancer Inst., 85:1657–1669, 1993.
9. Sherr, C. J. G1 phase progression: cycling on cue. Cell, 79:551–555, 1994.
10. Matsushime, H., Quelle, D. E., Shurtleff, S. A., Shibuya, M., Sherr, C. J., and Kato, J.-Y. D-type cyclin-dependent kinase activity in mammalian cells. Mol. Cell Biol., 14:2066–2076, 1994.
11. Gillett, C., Fantl, V., Smith, R., Fisher, C., Bartek, J., Dickson, C., Barnes, D., and Peters, G. Amplification and overexpression of cyclin D1 in breast cancer detected by immunohistochemical staining. Cancer Res., 54:1812–1817, 1994.
12. Jares, P., Fenandez, P. L., Campo, E., Nadal., A., Bosch, F., Aiza, G., Nayach, I., Traserra, J., and Cardesa, A. PRAD-1/Cyclin D1 gene amplification correlates with messenger RNA overexpression and tumor progression in human laryngeal carcinomas. Cancer Res., 54:4823–4827, 1994.
13. Michalides, R., van Veelen, N., Hart, A., Loftus, B., Wientjens, E., and Balm, A. Overexpression of cyclin D1 correlates with recurrence in a group of forty-seven operable squamous cell carcinomas of the head and neck. Cancer Res., 55:975–978, 1995.
14. Jiang, W., Kahn, S. M., Tomita, N., Zhang, Y.-J., Lu, S.-H., and Weinstein, B. I. Amplification and expression of the human cyclin D gene in esophageal cancer. Cancer Res., 52:2980–2983, 1992.
15. Naitoh, H., Shibata, J., Kawaguchi, A., Kodama, M., and Hattori, T. Overexpression and localization of cyclin D1 mRNA and antigen in esophageal cancer. Am. J. Pathol., 146:1161–1169, 1995.
16. Zhang, T., Nanney, L. B., Luongo, C., Lamps, L., Heppner, K. J., DuBois, R. N., and Beauchamp, R. D. Concurrent overexpression of cyclic D1 and cyclin-dependent kinase 4 (Cdk4) in intestinal adenomas from multiple intestinal neoplasia (Min) mice and human familial adenomatous polyposis patients. Cancer Res., 57:169–175, 1997.
17. SAS Institute Inc., SAS/STAT user guide, version 6 Cary N.C. SAS Institute Inc., 1990.
18. Kaplan, E. L., and Meier, P. Nonparametric estimation from incomplete observations. J. Am. Stat. Assoc., 53:457–481, 1958.
19. Carter, B. H., Piantadosi, S., and Isaacs, J. T. Clinical evidence for and implications of the multistep development of prostate cancer. J. Urol., 143:742–746, 1990.
20. Raghavan, D., Scher, H. I., Leibel, S. A., and Lange, P. Principles and practice of genitourinary oncology. Lippincott-Raven publishers. Philadelphia. New York, 1997.
21. Murphy, G. P., Mettlin, C., Menck, H., Winchester, D. P., and Davidson, A. M. The national survey of prostate cancer in the United States by the American College of Surgeons. J. Urol., 127:928–934, 1982.
22. Hall, M., and Peters, G. Genetic alterations of cyclins, cyclic-dependent kinases, and cdk inhibitors in human cancer. Adv. Cancer Res., 68:67–108, 1996.
23. Bartkova, J., Lukas, J., Strauss, M., and Bartek, J. Cyclic D1 oncoprotein aberrantly accumulates in malignancies of diverse histogenesis. Oncogene, 10:775–778, 1995.
24. Lammie, G. A., Fantl, V., Smith, R., Schuuring, E., Brookes, S., Michalides, R., Dickson, C., Arnold, A., and Peters, G. D11S287, a putative oncogene on chromosome 11q13, is amplified and expressed in squamous cell and mammary carcinomas and linked to BCL-1. Oncogene, 6:439–444, 1991.
25. Kallakury, B. V. S., Sheehan, C. E., Ambros, R. A., Fisher, H. A. G., Kaufman, R. P., and Ross, J. S. The prognostic significance of $p34^{cdc2}$ and cyclic D1 protein expression in prostate adenocarcinoma. Cancer, 80:753–763, 1997.
26. Jiang, W., Kahn, S. M., Zhou, P., Zhang, Y. J., Cacace, A. M., Infante, A. S., Doi, S., Santella, R. M., and Weinstein, I. B. Overexpression of cyclin D1 in rat fibroblasts causes abnormalities in growth control, cell cycle progression and gene expression. Oncogene, 8:3447–3457, 1993.
27. Quelle, D. E., Ashmun, R. A., Shurtleff, S. A., Kato, J. Y., Bar-Sagi, D., Roussel, M. F., and Sherr, C. J. Overexpression of mouse D-type cyclins accelerates G1 phase in rodent fibroblasts. Genes Dev., 7:1559–1571, 1993.

Fourth Series of Experiments

The INK4A gene maps to the region 9p21 and was initially described as encoding a 148 amino acid protein termed p16. The p16 protein associates exclusively with Cdk4 and Cdk6, inhibiting their complexation with D-type cyclins, and the consequent phosphorylation of pRB. This contributes to cell cycle arrest. The purpose of the present study was to evaluate patterns of p16 expression in a well characterized cohort of prostatic adenocarcinomas, while exploring potential associations between alterations of p16 and clinicopathological variables.

Normal and malignant tissues from 88 patients with prostate carcinoma were examined. In situ hybridization and immunohistochemistry assays were used to determine the status of the INK4A exon 1α transcripts and levels of p16 protein, respectively. Associations between altered patterns of expression and clinicopathological variables, including pre-treatment prostate-specific antigen (PSA) level, Gleason grade, pathologic stage, and hormonal status, were evaluated using the Mantel-Haenszel chi-square test. Biochemical (PSA) relapse after surgery was evaluated using the Kaplan-Meier method and the Log rank test.

The levels of p16 expression and INK4A exon 1α transcripts in normal prostate and benign hyperplastic tissues were undetectable. However, p16 nuclear overexpression was observed in 38 (43%) prostate carcinomas, while the remaining 50 (57%) cases showed undetectable p16 levels. Overexpression of p16 protein was found to correlate with increased INK4A exon 1α transcripts. Moreover, p16 overexpression was associated with a higher pre-treatment PSA level (P=0.018), the use of neoadjuvant androgen ablation (P=0.001), and a sooner time to PSA relapse after radical prostatectomy (P=0.002). These data suggest that p16 overexpression is associated with tumor recurrence and a poor clinical course in patients with prostate cancer.

The INK4A gene maps to the short arm of chromosome 9 (9p21), and was initially described as encoding a protein of Mr 15,845, termed p16. (1,2). The p16 protein forms binary complexes exclusively with Cdk4 and Cdk6, inhibiting their kinase activity and subsequent pRb phosphorylation during the $G_1$ phase of the cell cycle. (1,3). Additional complexity results from the presence of a second INK4A product termed $p19^{ARF}$. (4–6) The $p19^{ARF}$ protein has recently been shown to interact with mdm2 and to block mdm2-induced p53 degradation and transactivational silencing(7,8). The two products, p16 and $p19^{ARF}$, share exons 2 and 3 of the INK4A gene, but have distinct promoters and exon 1 units, exon 1α (p16) and exon 1β ($p19^{ARF}$) The INK4A gene is mutated in a wide variety of tumor cell lines and certain primary tumors (2, 9–14). In addition, methylation of the 5' CpG island of the exon 1α promoter region is a frequent mechanism of p16 inactivation in primary tumors (15, 16).

In prostate cancer the role of INK4A has not been well elucidated, though analyses utilizing microsatellite markers in the vicinity of the INK4A gene have revealed loss of heterozygosity in a subset of primary and metastatic prostate tumors (17). Unlike reports of other primary tumors, INK4A inactivation, either through deletions, mutations, or through promoter methylation, appears to be an infrequent event in prostate cancer (18–23). The present study utilizes immunohistochemical and in situ hybridization assays to examine patterns of p16 expression in a well characterized cohort of prostate cancer patients treated with radical retropubic prostatectomy. Associations between altered p16 phenotypes and clinicopathological variables were also studied to further define their potential implications in prostate cancer.

Experimental Details
Experimental Details for Fourth Series of Experiments
Material and Methods Patient Characteristics and Tissues. A cohort of patients with prostatic adenocarcinoma undergoing radical prostatectomy at the Memorial Sloan-Kettering Cancer Center from 1990–1991 was retrospectively evaluated. A total of 88 patients had adequate clinical follow-up and available pathological materials. The median age at the time of surgery was 65 years (range 46–74 years). The median follow-up time was 64.5 months (range 10–94 months). Formalin-fixed, paraffin-embedded prostate tissues were obtained from the Department of Pathology. Representative hematoxylin-eosin stained sections were examined to evaluate the histopathological characteristics of each tissue section.

Clinicopathologic parameters examined included pre-treatment PSA, pathologic stage (24) and Gleason grade (25), both determined based on the radical prostatectomy specimen. Hormonal status of the patients was also evaluated. A portion of the cohort (34 patients—39%) was treated with neoadjuvant androgen ablation and were defined as hormone-treated. Patients who did not receive neoadjuvant therapy were defined as hormone naive. Additionally, biochemical relapse was examined. Relapse was defined as an elevation in the serum PSA level in a patient who had previously demonstrated an undetectable PSA level post-prostatectomy. That is, only patients who had an undetectable PSA level after surgery were included in the cohort, as this indicated that the surgical resection was complete and the patient was free of disease. Patients who had PSA relapse were classified as treatment failures with tumor recurrence.

Immunohistochemistry. An avidin-biotin immunoperoxidase assay was performed on formalin-fixed, paraffin-embedded tissue sections. Deparaffinized sections were treated with 1% $H_2O_2$ in order to block endogenous peroxidase activity. Sections were subsequently immersed in boiling 0.01% citric acid (pH 6.0) in a microwave oven for 15 minutes to enhance antigen retrieval, allowed to cool, and incubated with 10% normal horse serum (Organon Tecknika Corp, Westchester, Pa.), to block non-specific tissue immunoreactivities. A well characterized antibody to p16 (Ab-1, Oncogene Research Products, Cambridge, Mass.; 2 ug/ml final concentration) was then incubated overnight at 4° C. Biotinylated horse anti-mouse IgG antibodies (Vector Laboratories, Inc., Burlingame, Calif.; 1:25 final dilution) were utilized as the secondary reagents. This was followed by avidin-biotin immunoperoxidase complexes (1:25, Vector laboratories, Inc.) for 30 minutes. Diaminobenzidine was used as the final chromogen and hematoxylin was used as the nuclear counterstain. Immunoreactivities, assessed in tissue sections from a single representative block in each case, were classified as a continuum of data from undetectable levels or (0%) to homogenous staining levels (100%). Data was independently obtained by two observers, with minor inter-observer variability which was resolved by review of the problem cases. Tumors were grouped into two categories defined as follows: Group A ($\leq$5% nuclear immunoreactivity in tumor cells) and Group B (>5% nuclear immunoreactivity in tumor cells).

In Situ Hybridization. Primers specific for the exon 1α sequence of the INK4A gene were utilized to create digoxigenin-labeled probes for in situ hybridization. Probes were cloned into a PCR-Script recombinant plasmid (Stratagene, La Jolla, Calif.). Plasmid DNA (1ug) was linearized using BamHI and XhoI. Antisense and sense riboprobes were generated from in vitro transcription of the linearized DNA using T7 and T3 RNA polymerases, respectively. Transcription was sustained for 2 hours at 37° C. in 1× transcription buffer (Boehringer Mannheim, Indianapolis, Ind.), 20 U of RNAse inhibitor, 10 mmol/L each of ATP, GTP, CTP, 6.5 mmol/L UTP and 3.5 mmol/L digoxigenin-UTP. Deparaffinized tissue sections were rinsed in water and PBS for 10 minutes. The slides were digested with Proteinase K (50 ug/ml) for 18 minutes at 37° C. in PBS, and post-fixed at 4° C. in a freshly prepared. solution of 4% paraformaldehyde in PBS for 5 minutes. Prehybridization was done for 30 minutes at room temperature (RT) in 50% formamide and 2× sodium chloride/sodium citrate (SSC). The hybridization buffer consisted of 50% deionized formamide (v/v), 10% dextran sulphate (50% stock solution), 2×SSC (20× stock solution), 1% SDS (10% stock solution), and 0.25 mg/ml of herring sperm DNA (10 mg/ml).

Hybridization was performed overnight at 45° C. applying 10 pmol/L digoxigenin-labeled riboprobe in 50 ul of hybridization buffer per section under a coverslip. The coverslips were removed and the slides were washed in pre-warmed 2×SSC for 20 minutes at 42° C. twice, followed by washes in pre-warmed 1×SSC and 0.5×SSC at 42° C. for 20 minutes. After these washes the slides were incubated in normal sheep serum diluted in buffer pH 7.5 and successively in the same buffer with anti-digoxigenin-AP antibody (Boehringer Mannheim) at a dilution of 1:500 for 1 hour at RT. The visualization was accomplished by nitro-blue tetrazolium 5-bromo-4-chloro-3-indoylphosphate. The slides were counterstained with methyl green and mounted.

INK4A exon-1α transcript levels were examined in a subgroup of 21 cases. Consecutive tissue sections were used to analyze p16 protein by immunohistochemistry and INK4A exon-1α transcript levels by in situ hybridization. As in the immunohistochemical analysis, tumors were grouped into two categories defined by the absence ($\leq$5% tumor cells with cytoplasmic staining) or presence (>5% tumor cells with cytoplasmic staining) of transcripts.

Statistical Methods. The statistical analyses of the data from the 88 primary prostate cancer patients were conducted as follows. The response variable, time to PSA relapse, was defined as the time from radical prostatectomy to the time of first detectable PSA measurement. Patients who did not achieve a non-measurable PSA after radical prostatectomy were excluded from the analysis. Patients who were still alive at the time of analysis without relapse were censored at the date of last follow-up. The baseline variables examined were PSA measurement at time of diagnosis, hormone status, Gleason score (hormone naive patients only), stage of disease, and percent p16 expression.

Associations between p16 expression and different categorical variables (hormone status, tumor grade, tumor stage, and pretreatment PSA levels) were assessed by Mantel-Haenszel chi-square test. Continuous variables, such as pre-treatment PSA, not known to follow a particular distribution were compared between two or more groups using Wilcoxon non-parametric tests. The Cox proportional hazards model was used to examine the multivariate relationship between PSA relapse-free time from prostatectomy and the baseline variables listed above. The final model was determined using the "all subsets" procedure in SAS PHREG and the Score criterion (26). As normal and benign tissues showed little to no p16 expression, positive expression was described as >5% nuclear expression. This cutpoint was specified a priori and used for the subsequent statistical analysis. Immunohistochemical and in situ hybridization studies were completed, analyzed, and recorded blind to clinical information. Kaplan-Meier estimates of relapse-free survival stratified by p16 classification were evaluated. The LIFETEST procedure in SAS was used to generate the Kaplan-Meier estimates and the resulting survival curves (26, 27). The Log rank test was used to test the hypothesis of no survival differences between p16 positive and p16 negative populations.

Experimental Results

Experimental Results for the Fourth Series of Experiments

The normal human prostate displayed undetectable levels of p16 protein and INK4A exon 1α transcripts in ductal and acinar epithelial cells. A lack of p16 immunoreactivity in these cells was observed in hormone-treated and hormone naive cases. Fibromuscular stroma cells also showed undetectable exon 1α transcripts levels. A similar negative pattern of p16 expression was observed upon the examination of prostatic tissue affected with benign hyperplasia (FIG. 10).

To determine the frequency and potential clinical implications of p16 alterations in prostate cancer, we analyzed a cohort of 88 primary prostate carcinomas. Two patterns of p16 protein expression were noted. We observed that 50 of the 88 cases (57w) had very low ($\leq$5% nuclear immunoreactivity; 7 cases) or undetectable (43 cases) levels of p16 protein expression (Group A) (FIG. 11A). In a subgroup of these cases we also performed in situ hybridization assays, which revealed that all cases had undetectable INK4A exon 1α transcripts (FIG. 11B). However, we noted that 38 of the 88 cases (43%) displayed nuclear staining with anti-p16 specific antibodies (Group B) (FIG. 1C). Immunoreactivities in tumor cells were further stratified into three categories: 6% to 29% nuclear staining (n=11 cases); 30% to 59% nuclear staining (n=15 cases); and 60% to 100% nuclear staining (n=12 cases). In a subset of these patients, we also conducted in situ hybridization assays with the INK4A exon 1α specific probe. All cases displaying positive immunoreactivities also displayed moderate to high levels of exon 1α transcripts (FIG. 11D).

Table 3 summarizes the associations between p16 phenotypes and clinicopathological variables, which were assessed by Chi-square analyses. Immunohistochemical detection of p16 was not associated with Gleason grade, described as either low (Gleason grade 4–6) or high (Gleason grade 7–10) (P=0.153). Similarly, no association was observed between p16 nuclear expression and pathologic stage, defined as organ-confined ($T_1$, $T_2$) and non organ-confined ($T_3$, $T_4$, or lymph node+) (P=0.087). However, there was a strong association between p16 nuclear expression and pre-treatment PSA levels, based on cutoff points of <4, 4–10, and >10 ng/ml (P=0.018). A similar result was observed when PSA was assessed as a continuous variable (P=0.01). In addition, we noted a significant correlation between p16 nuclear expression and the use of neoadjuvant androgen ablation (P=0.001).

TABLE 3

Association of p16 Immunoreactivity with Tumor Grade, Hormonal Status, Tumor Stage, and Preoperative PSA Levels

| | Number of Subjects | P16 Immunoreactivity (& of patients) | | |
|---|---|---|---|---|
| | | $\leq$5% | 5% | p - value |
| All Subjects | 88 | 50 (57%) | 38 (43%) | |
| Gleason Grade* | 82 | | | |
| <7 | 30 (37) | 24 (80) | 6 (20) | p = 0.153 |
| $\geq$7 | 18 (22) | 11 (61) | 7 (39) | |
| unable to evaluate | 34 (41) | | | |
| Hormonal Status | 88 | | | |
| hormone naive | 54 (61) | 40 (74) | 14 (26) | p = 0.001 |
| hormone-treated | 34 (39) | 10 (29) | 24 (71) | |
| Pathologic Stage | 88 | | | |
| $T_2$ | 53 (60) | 34 (64) | 19 (36) | p = 0.087 |
| $\geq T_3$ | 35 (40) | 16 (46) | 19 (54) | |
| Pretreatment PSA (ng/ml) | 88 | | | |
| <4.0 | 18 (20) | 14 (78) | 4 (22) | |
| 4–10 | 29 (33) | 19 (66) | 10 (34) | p = 0.018 |
| >10 | 41 (47) | 17 (41) | 24 (59) | |

*Grading is based on the radical prostatectomy specimen. Patients who had received neoadjuvant androgen therapy were unable to be graded consistently. Six patients did not have Gleason grade information and were excluded from this analysis.

A strong association was also found between p16 nuclear overexpression and tumor recurrence, as defined by biochemical (PSA) relapse. Increasing p16 expression correlated with an increased relative hazard of relapse, suggesting a continuous relationship of the data. Overall, tumor recurrence was observed in 34 of 88 cases (39%). Thirteen of 50 cases (26%) with undetectable-to-low p16 expression (Group A) developed tumor recurrence. However, tumor recurrence was observed in 21 of 38 cases (55%) with p16 nuclear overexpression (Group B) (P=0.002) (FIG. 12). Nevertheless, in a multivariate analysis adjusted for tumor grade, pre-treatment PSA, and pathologic stage, overexpression of p16 did not contribute prognostic information over pre-treatment PSA, the strongest independent predictor of tumor recurrence.

Experimental Discussion for the Fourth Series of Experiments

Normal prostate tissues display undetectable levels of p16 protein and INK4A exon 1α transcripts. It has been reported that p16 expression is low to undetectable in most normal human tissues analyzed (15, 28, 29). In support of these observations, there are relatively low and near-constant levels of p16 protein and mRNA throughout the cell cycle of normal lymphocytes in culture (30). The lack of p16 expression in hyperplastic glands parallels that of normal prostatic tissue. Based on these data, it is our hypothesis that these negative p16 phenotypes reflect basal physiologic levels of p16.

Primary prostatic adenocarcinomas revealed two distinct p16 phenotypes. Most tumors were found to have undetectable or very low levels of p16 protein expression (Group A—57% of cases). This was associated with low levels or absence of INK4A exon 1α transcripts. Another group of tumors showed elevated p16 protein expression (Group B—43%) which was consistently associated with increased INK4A exon 1α transcripts. These findings suggest an upregulation of the INK4A-α gene, resulting in p16 protein overexpression. Patients in Group B had a more aggressive course, demonstrated by high levels of pre-treatment PSA (P=0.018) and a sooner time to biochemical (PSA) relapse (P=0.002). A worse prognosis for Group B is also revealed by the trending association of p16 overexpression with higher pathologic stage.

The negative phenotype observed in Group A might correspond to the normal physiologic state, reflecting low-to-undetectable p16 levels. Alternatively, it could be related to mutations affecting the INK4A gene, especially homozygous deletions, or methylation of the INK4A exon 1α promoter region. Nevertheless, it has been reported that these events are infrequent in prostate cancer (17–23). Furthermore, it appears the tumors with INK4A mutations have a more aggressive clinical course (31–33). Contrary to this, in the present study, we observed that Group A patients had a less aggressive behavior than Group B patients. For these reasons, we hypothesize that the negative phenotype observed in Group A is more likely a reflection of the normal physiologic state.

The up-regulation of the INK4A-α gene, resulting in the overexpression of p16 protein, may develop through different mechanisms. An association between increased p16 transcript and protein levels occur in tumor cell lines and certain primary neoplasms that lack functional pRb (1, 34–37). Moreover, p16-mediated inhibition of cell cycle progression appears to be dependent upon functional pRb (38, 39). These data support an association between p16 and pRb, where absence of functional pRb limits p16 activity and possibly promotes INK4A-α upregulation. Alternatively, enhanced activation of the INK4A-α gene may occur. E2F1, a direct activator of the INK4A exon 1β promoter, does not appear to directly activate INK4A-α transcription (40). However, evidence does exist for an indirect effect, as E2F1 overexpression has been reported to markedly increase p16 transcripts and p16-related CKI activity (41). Overexpression of cyclin D1 and/or of Cdk4 may also influence p16 expression, through a compensatory feedback loop where deregulation of cyclin D/Cdk4 complexes results in increased levels of p16 protein (28, 42). In summary, it appears that an altered RB axis could trigger p16 overexpression in certain systems.

Cellular stress produced by replicative senescence (43–45), hyperthermia (46), and UV irradiation (47) has been reported to trigger p16 overexpression. In the present study, another type of cellular stress, androgen ablation, may account in part for this observed phenomenon. A subset of patients were treated with neoadjuvant androgen ablation, a strategy reported to decrease the incidence of positive surgical margins after prostatectomy (48). In the present study, p16 overexpression was observed in 71% of hormone-treated versus 26% of hormone-naive patients (P=0.001). These data suggest that p16 expression may be enhanced by androgen depletion. Androgens are known to modulate the expression of other CKI's such as p27 and p21 (49). In addition, it has been reported that the presence of androgens triggers downregulation of p16 in LNCaP cells (50), a finding consistent with our observation of p16 overexpression in cases of androgen ablation. It is also possible that the association between p16 expression and androgen ablation may, in part, reflect staging bias by clinicians. In this setting, patients thought to have advanced disease may have been treated with neoadjuvant therapy.

Based on the the above referred data, it is our working hypothesis that p16 overexpression in prostate cancer represents an altered phenotype, which identifies a subgroup of patients with a higher likelihood of post surgical failure and tumor recurrence. In support of this postulate, a preliminary report in prostate cancer has demonstrated an association between p16 overexpression and poor outcome, as related to biochemical failure (51). In addition, p16 overexpression has been associated with tumor progression and a poor prognosis in ovarian (52) and breast cancers (37). Though p16 acts as a negative cell cycle regulator, specific mechanisms may contribute to its altered expression, overcoming p16-mediated tumor suppressor activities. Ongoing studies may elucidate mechanisms of p16 overexpression relative to androgen depletion and/or alterations in the RB axis.

References for the Fourth Series of Experiments.

1. Serrano M., Hannon G. J.,and Beach D. "A new regulatory motif in cell cycle control causing specific inhibition of cyclinD-cdk4." *Nature*, 366:704–707 (1993).
2. Kamb A., Gruis N., Weaver-Feldhaus J., Liu Q., Harshman K., Tavtigian S., Stockert E., Day R. 3rd, Johnson B., and Skolnick M. "A cell cycle regulator potentially involved in genesis of many tumor types." *Science*, 264:436–440 (1994).
3. Quelle D., Ashmun R., Hannon G., Rehberger P., Trono D., Richter H., Walker C., Beach D., Sherr C., and Serrano M. "Cloning and characterization of murin P16$^{INK4a}$ and p15$^{INK4b}$ genes." *Oncogene*, 11:635–645 (1995).
4. Quelle D., Zindy F., Ashmun R., and Sherr C. "Alternative reading frames of the INK4a tumor suppressor gene encode two unrelated proteins capable of inducing cell cycle arrest." *Cell*, 83:993–1000 (1995).
5. Mao L., Merlo A., Bedi G., Shapiro G., Edwards C., Rollins B., and Sidransky D. "A novel p16$^{INK4A}$ transcript." *Cancer Res.*, 55:2995–2997 (1995).
6. Stone S., Jiang P., Dayananth P., Tavtigian S., Katcher H., Parry D., Peters G., and Kamb A. "Complex structure and regulation of the P16 (MTS1) locus." *Cancer Res.* 55:2988–2994 (1995).
7. Pomerantz J., Schreiber-Agus N., Liegeois N. J., Silverman A., Alland L., Chin L., Potes J., Chen K., Orlow I., 7. Lee H. W., Cordon-Cardo C., and DePinho R. "The Ink4a tumor suppressor gene product, p19$^{Arf}$, interacts with MDM2 and neutralizes MDM2's inhibition of p53." *Cell*, 92:713–723 (1998).

8. Zhang Y., Xiong Y., and Yarbrough W. "ARF promotes MDM2 degradation and stabilized p53: ARF-INK4a locus deletion impairs both the Rb and p53 tumor suppression pathways." *Cell*, 92:725–734 (1998).

9. Jen J., Harper J., Bigner S., Signer D., Papadopoulos N., Markowitz S., Willson J., Kinzler K., and Vogelstein B. "Deletion of p16 and p15 genes in brain tumors." *Cancer Res.* 54:6353–6358 (1994).

10. Spruck C. III, Gonzalez-Zulueta M., Shibata A., Simoneau A., Lin M., Gonzales F., Tsai Y., and Jones P. "p16 gene in uncultured tumours." *Nature*, 370:183–184 (1994).

11. Orlow I., Lacombe L., Hannon G., Serrano M., Pellicer I., Dalbagni G., Reuter V., Zhang Z., Beach D., and Cordon-Cardo C. "Deletion of the p16 and p15 genes in human bladder tumors." *J. Natl. Cancer Inst.*, 87:1524–1529 (1995).

12. Reed A., Califano J., Cairns P., Westra W., Jones R., Koch W., Ahrendt S., Eby Y., Sewell D., Nawroz H., Bartek J., and Sidransky D. "High frequency of p16 (CDKN2/MTS1/INK4A) inactivation in head and neck squamous cell carcinoma." *Cancer Res.*, 56:3630–3633 (1996).

13. Washimi O., Nagatake M., Osada H., Ueda R., Koshikawa T., Seki T., Takahashi T., and Takahashi T. "In vivo occurrence of p16 (MTS1) and p15 (MTS2) alterations preferentially in non-small cell lung cancers" *Cancer Res.*, 55:514–517 (1995).

14. Takeuchi S., Bartram C., Seriu T., Miller C., Tobler A., Janssen J., Reiter A., Ludwig W., Zimmermann M., Schwaller J., Lee E., Miyoshi I., and Koeffler H P. "Analysis of a family of cyclin-dependent kinase inhibitors: p15/MTS2/INK4B, p16/MTS1/INK4A, and p18 genes in acute lymphoblastic leukemia of childhood."*Blood*, 86:755–760 (1995).

15. Gonzales-Zulueta M, Bender C, Yang A, Nguyen T, Beart R, Van Tornout J, and Jones P. "Methylation of the 5' CpG island of the p16/CDKN2 tumor suppressor gene in normal and transformed human tissues correlates with gene silencing." *Cancer Res.*, 55:4531–4535 (1995).

16. Merlo A, Herman J, Mao L, Lee D, Gabrielson E, Burger P, Baylin S, and Sidransky D. "5' CpG island methylation is associated with transcriptional silencing of the tumor suppressor p16/CDKN2/Mts1 in human cancers." *Nature Med.*, 1:686–692 (1995).

17. Jarrard D, Bova S, Ewing C, Pin S, Nguyen S, Baylin S, Cairns P, Sidransky D, Herman J, and Isaacs W. "Deletional, mutational, and methylation analyses of CDKN2 (p16/MTS1) in primary and metastatic prostate cancer." *Genes, Chrom. & Cancer*, 19:90–96 (1997).

18. Mangold K, Takahashi H, Brandigi C, Wada T, Wakui S, Furusato M, Boyd J, Chandler F, and Allsbrook W. "p16 (CDKN2/MTS1) gene deletions are rare in prostatic carcinomas in the United States and Japan." *J. Urol.*, 157:1117–1120 (1997).

19. Park D, Wilczynski S, Pham E, Miller C, and Koeffler HP. "Molecular analysis of the INK4 family of genes in prostate carcinomas." *J. Urol.*, 157: 1995–1999, (1997).

20. Tamimi Y, Bringuler P, Smit F, van Bokhoven A, Debruyne F, and Schalken J. "p16 mutations/deletions are not frequent events in prostate cancer." *Brit. J. Cancer*, 74:120–122 (1996).

21. Chen W, Weghorst M, Sabourin C, Wang Y, Wang D, Bostwick D, and Stoner G. "Absence of p16/MTS1 gene mutations in human prostate cancer." *Carcinogenesis*, 17:2603–7 (1996).

22. Jarrard D, Bova S, Ewing C, Pin S, Nguyen S. Baylin S, Cairns P, Sidransky D, Herman J, and Isaacs W. "Deletional, mutational, and methylation analyses of CDKN2 (p16/MTS1) in primary and metastatic prostate cancer." *Genes, Chrom. & Cancer*, 19:90–96 (1997).

23. Gu K, Mes-Masson A M, Gauthier J, and Saad F. "Analysis of the p16 tumor suppressor gene in early-stage prostate cancer." *Mol. Carcinogenesis*, 21:164–170 (1998).

24. Schroder F, Hermanek P, Denis L, Fair W, Gospodarowicz M, and Pavone-Macaluso M. "The TNM classification of prostate cancer." *Prostate*, 4:129–38 (1992).

25. Gleason D and Mellinger G. "Prediction of prognosis for prostatic adenocarcinoma by combined histological grading and clinical staging." *J. Urol*, 111:58–64 (1974).

26. SAS Institute Inc. SAS/STAT User Guide., Version 6. Cary, N.C.: SAS Institute Inc. (1990).

27. Kaplan E L, Meier P. Nonparametric estimation from incomplete observations. JASA, 53:457–481 (1958).

28. Yao J, Pollock R, Lang A, Tan M, Pisters W, Goodrich D, El-Naggar A, and Yu D. "Infrequent mutation of the p16/MTS1 gene and overexpression of cyclin-dependent kinase 4 in human primary soft-tissue sarcoma." *Clin. Cancer Res.*, 4:1065–1070 (1998).

29. Shapiro G, Edwards C, Kobzik L, Lodleski J, Richards W, Sugarbaker D, and Rollins B. "Feciprocal Rb inactivation and p16INK4 expression in primary lung cancers and cell lines." *Cancer Res.*, 55:505–509 (1995).

30. Soucek T, Pusch O, Hengstschlager-Ottnad E, Wawra E, Bernaschek G, and Hengstschlager M. "Expression of the cyclin-dependent kinase inhibitor p16 during the ongoing cell cycle." *FEBS Letters*, 373:164–169 (1995).

31. Taga S, Osaki T, Ohgami A, Imoto H, Yoshimatsu T, Yoshino I, Yano K, Nakanishi R, Ichiyoshi Y, and Yasumoto K. "Prognostic value of the immunohistochemical detection of p16INK4 expression in nonsmall cell lung carcinoma." *Cancer*, 80:389–95 (1997).

32. Garcia-Sanz R, Gonzalez M, Vargas M, Chillon M, Balanzategui A, Barbon M, Flores M, and San Miguel J. "Deletions and rearrangements of cyclin-dependent kinase 4 inhibitor gene p16 are associated with poor prognosis in B cell non-Hodgkin's lymphomas." *Leukemia*, 11: 1915–20, (1997).

33. Straume O and Akslen L. "Alterations and prognostic significance of p16 and p53 protein expression in subgroups of cutaneous melanoma." *Int. J. Cancer* 74:535–539 (1997).

34. Parry D, Bates S, Mann D J, and Peters G. "Lack of cyclin D-cdk complexes in Rb-negative cells correlates with high levels of p16INK4/MTS1 tumour suppressor gene product." *EMBO J.*, 14:503–511 (1995).

35. Ueki K, Ono Y, Henson J W, Efird J T, von Deimling A, Louis D N. "CDKN2/p16 or RB alterations occur in the majority of glioblastomas and are inversely correlated." *Cancer Res.*, 56:150–153 (1996).

36. Li Y, Nichols M, Shay J, and Xiong Y. "Transcriptional repression of the D-type cyclin-dependent kinase inhibitor p16 by the retinoblastoma susceptibility gene product pRb." *Cancer Res.*, 54:6078–6082 (1994).

37. Dublin E, Patel N, Gillett C, Smith P, Peters G, and Barnes D. "Retinoblastoma and p16 proteins in mammary carcinoma: their relationship to cyclin D1 and histopathological parameters." *Int. J. Cancer*, 79:71–5 (1998).

38. Lukas J, Parry D, Aagaard L, Mann DJ, Bartkova J, Strauss. M, Peters G, and Bartek J. "Retinoblastoma-protein-dependent-cell-cycle inhibition by the tumour suppressor p16." Nature, 375:503-506 (1995).

39. Craig C, Kim M, Ohri E, Wersto R, Katayose D, Li Z, Choi Y, Mudahar B, Srivastava S, Seth P, and Cowan K. "Effects of adenovirus-mediated p16INK4A expression on cell cycle arrest are determined by endogenous p16 and Rb status in human cancer cells." *Oncogene,* 16:265–272 (1998).
40. Robertson K and Jones P. "The human ARF cell cycle regulatory gene promoter is a CpG island which can be silenced by DNA methylation and down-regulated by wild-type p53." *Mol. Cell. Biol.,* 18:6457–6473 (1998).
41. Khleif S, DeGregori J, Yee C, Otterson G, Kaye F, Nevins J, and Howley P. "Inhibition of cyclin D-CDK4/CDK6 activity is associated with an E2F-mediated induction of cyclin kinase inhibitor activity." *Proc. Natl. Acad. Sci. USA,* 93:4350–4354 (1996).
42. Burns K, Ueki K, Jhung S, Koh J, and Louis D. "Molecular genetic correlates of p16 cdk4, and pRb immunohistochemistry in glioblastomas." *J. Neuropathol. & Exp. Neurology,* 57:122–130 (1998).
43. Hara E, Smith R, Parry D, Tahara H. Stone S, and Peters G. "Regulation of p16 CDKN2 expression and its implications for cell immortalization and senescence." *Mol. Cell. Biol.,* 16:859–867 (1996).
44. Palmero I, McConnel B, Parry D, Brookes S, Hara E, Bates S, Jat P, and Peters G. "Accumulation of p16INK4a in mouse fibroblasts as a function of replicative senescence and not of retinoblastoma gene status." *Oncogene,* 15:495–503 (1997).
45. Yeager T, DeVries S, Jarrard D, Kao C, Nakada S, Moon T, Bruskewitz R, Stadler W, Meisner L, Gilchrist K, Newton M, Waldman F, and Reznikoff C. "Overcoming cellular senescence in human cancer pathogenesis."*Genes & Devel.,* 12:163–174 (1998).
46. Valenzuela M T, Nunez M I, Villalobos M, Siles E, McMillan T, Pedraza V, and Almodovar R. "A comparison of p53 and p16 expression in human tumor cells treated with hyperthermia or ionizing radiation." *Int. J. cancer,* 72:307–312 (1997).
47. Wang X, Gabrielli B, Milligan A, Dickinson J, Antalis T, and Ellem K. "Accumulation of p16$^{CDKN2A}$ in response to ultraviolet irradiation correlates with a late S-G$_2$-phase cell cycle delay." *Cancer Res.,* 56:2510–2514 (1996).
48. Witjes W, Schulman C, and Debruyne F. "Preliminary results of a prospective randomized study comparing radical prostatectomy versus radical prostatectomy associated with neoadjuvant hormonal combination therapy in T2-3 N0 M0 prostatic carcinoma. The European Study Group on Neoadjuvant Treatment of Prostate Cancer." *Urology,* 49S:65–9 (1997).
49. Kokontis J, Hay N, and Liao S. "Progression of LNCaP prostate tumor cells during androgen deprivation: Hormone-independent growth, repression of proliferation by androgen, and role for p27$^{Kip1}$ in androgen-induced cell cycle arrest." *Mol. Endocrinol.,* 12:941–953 (1998).
50. Lu S, Tsai S Y, and Tsai M-J. "Regulation of androgen-dependent prostatic cancer cell growth: androgen regulation of CDK2, CDK4, and CKI p16 genes." *Cancer Res.,* 57:4511–4516 (1997).
51. Halvorsen O J, Hostmark J, Haukass, Hoisaeter P, and Akslen L. "Prognostic importance of p16 and CDK4 proteins in localized prostate cancer." *Proc. Am. Assoc. Cancer Res.,* 38:526 (1997).
52. Dong Y, Walsh M, McGuckin M, Gabrielli B, Cummings M, Wright R G, Hurst T, Khoo S K, and Parsons P. "Increased expression of cyclin-dependent kinase inhibitor 2 (CDKN2A) gene product p16$^{ink4A}$ in ovarian cancer is associated with progression and unfavorable prognosis." *Int. J. Cancer,* 74:57–63 (1997).

What is claimed is:

1. A method for determining the likelihood that a prostate hyperplasia is a benign prostate hyperplasia comprising:

(a) obtaining an appropriate sample of the hyperplasia;

(b) determining the amount of p27 RNA present in the sample; and (c) comparing the amount so determined to the amount of p27 RNA present in a normal prostate sample, a decreased amount of p27 RNA in the hyperplasia sample relative to the normal prostate sample indicating a likelihood that the hyperplasia is benign prostate hyperplasia.

2. The method of claim 1, further comprising determining and comparing the amounts of p27 protein expressed in the hyperplasia sample and normal prostate sample, wherein this additional step is performed either before or after determining the amount of p27 RNA present in the hyperplasia and normal prostate samples.

* * * * *